United States Patent
Harris et al.

(10) Patent No.: US 7,035,716 B2
(45) Date of Patent: Apr. 25, 2006

(54) ACTIVE-CONSTRAINT ROBOTS

(75) Inventors: Simon James Harris, London (GB); Brian Lawrence Davies, London (GB); Matjaz Jakopec, London (GB)

(73) Assignee: The Acrobot Company Limited, London (GB)

(*) Notice: Subject to any disclaimer, the term of this patent is extended or adjusted under 35 U.S.C. 154(b) by 303 days.

(21) Appl. No.: 10/470,314

(22) PCT Filed: Jan. 29, 2002

(86) PCT No.: PCT/GB02/00365

§ 371 (c)(1),
(2), (4) Date: Dec. 19, 2003

(87) PCT Pub. No.: WO02/060653

PCT Pub. Date: Aug. 8, 2002

(65) Prior Publication Data

US 2004/0128026 A1    Jul. 1, 2004

(30) Foreign Application Priority Data

Jan. 29, 2001  (GB) .................................. 0102248
Jan. 29, 2001  (GB) .................................. 0102251
Jan. 29, 2001  (GB) .................................. 0102253

(51) Int. Cl.
G06F 19/00    (2006.01)

(52) U.S. Cl. ................. 700/245; 700/260; 318/568.1; 600/102; 606/130

(58) Field of Classification Search ............... 700/245, 700/260; 318/568.1; 600/102; 606/130

See application file for complete search history.

(56) References Cited

U.S. PATENT DOCUMENTS

| 5,694,013 | A  |   | 12/1997 | Stewart et al. |
|-----------|----|---|---------|----------------|
| 5,802,494 | A  | * | 9/1998  | Kuno ............................. 705/2 |
| 5,973,678 | A  |   | 10/1999 | Stewart et al. |
| 6,131,097 | A  |   | 10/2000 | Peurach et al. |
| 6,158,136 | A  |   | 12/2000 | Götz et al. |
| 6,714,841 | B1 | * | 3/2004  | Wright et al. ............... 700/259 |

(Continued)

FOREIGN PATENT DOCUMENTS

EP    0 595 291 A1    5/1994

(Continued)

OTHER PUBLICATIONS

Tendick et al., Human-machine interfaces for minimilly invasive surgery, 1997, IEEE, p. 1-6.*

(Continued)

*Primary Examiner*—Thomas G. Black
*Assistant Examiner*—McDieunel Marc
(74) *Attorney, Agent, or Firm*—Wallenstein Wagner & Rockey, Ltd.

(57) ABSTRACT

An active-constraint robot (4), particularly for surgical use, is controlled by means of a series of motorized joints to provide a surgeon with real-time tactile feedback of an operation in progress. The robot system holds, in memory, a series of constraint surfaces beyond which it would be dangerous for the surgeon to go, and a resistive force is applied to the cutting tool (14) as the surgeon approaches any such surface. To improve the overall quality of feedback experienced by the surgeon, the resistive force applied to the cutting tool (14) depends upon the point of intersection (I) between the force factor applied by the surgeon and the surface. Further improvements are achieved by adjusting the tangential resistive force, when the tool is adjacent to the surface, in dependence upon the surrounding shape of the surface.

28 Claims, 20 Drawing Sheets

U.S. PATENT DOCUMENTS

| | | | |
|---|---|---|---|
| 6,799,065 B1 * | 9/2004 | Niemeyer | 600/407 |
| 6,879,880 B1 * | 4/2005 | Nowlin et al. | 700/260 |
| 6,905,491 B1 * | 6/2005 | Wang et al. | 606/1 |
| 6,933,695 B1 * | 8/2005 | Blumenkranz | 318/568.11 |
| 6,965,812 B1 * | 11/2005 | Wang et al. | 700/258 |
| 2003/0050649 A1 * | 3/2003 | Brock et al. | 606/130 |
| 2003/0109780 A1 * | 6/2003 | Coste-Maniere et al. | 600/407 |
| 2005/0228440 A1 * | 10/2005 | Brock et al. | 606/205 |

FOREIGN PATENT DOCUMENTS

| | | |
|---|---|---|
| GB | 2298931 A | 9/1996 |
| WO | WO 97/00649 A1 | 1/1997 |
| WO | WO 99/37220 A1 | 7/1999 |
| WO | WO 00/60571 A1 | 10/2000 |

OTHER PUBLICATIONS

Brian, Robotics in Minimilly invasive surgey, 1995, IEEE, p. 5-1-5/2.*

Wapler et al., Controlling miniature robotic systems in minimally invasive surgey, 1994, Internet, p. 711-716.*

Tzafestas et al., VR-based teleoperation of a mobile robotic assistant: Progress report, 2000, Internet, p. 1-23.*

International Search Report for PCT/GB02/00365 mailed Feb. 4, 2003.

Search Report under Section 17 from the UK Patent Office for Application No. GB 01/02248.2 (date of search May 1, 2001).

Search Report under Section 17 from the UK Patent Office for Application No. GB 01/02253.2 (date of search Jun. 26, 2001).

Search Report under Section 17 from the UK Patent Office for Application No. GB 01/02251.6 (date of search May 1, 2001).

MICCAI'99, Second International Conference, Cambridge UK, 1999, pp. 1116-1124, Intra-operative application of a robotic knee surgery system, Harris S J, Jakopec L, Cobb L, Davies B L.

8th International Conference on Advanced Robotics, Monterey CA USA, 1997, pp. 173-178, ACROBOT using robots and surgeons synergistically in knee surgery, Davies B L, Fan K L, Hibberd R D, Jakopec M, Harris S J.

Robotic Knee Surgery, Davies and Hibberd, 1997. http://www.me.ic.ac.uk/department/review97/case/caserr27.html.

* cited by examiner

ACTIVE-CONSTRAINT ROBOTS

CROSS-REFERENCE TO RELATED APPLICATIONS

This Application is the U.S. National Stage of International Application No. PCT/GB02/00365, with an international filing date of Jan. 29, 2002, now pending, claiming priority from Great Britian Application Nos. GB01/02248.2, GB01/02253.2 and GB01/02251.6, all with a filing date of Jan. 29, 2001, now pending, and herein incorporated by reference.

TECHNICAL FIELD

The present invention relates to active-constraint robots, and to methods of controlling such robots.

SUMMARY OF THE INVENTION

According to one aspect of the present invention there is provided a method of controlling an active-constraint robot, comprising the steps of: providing an active-constraint robot including a tool for operating on an element and at least one drive unit for controlling movement of the tool; providing a model including a NURBS surface describing at least one surface of the element to be operated on by the tool; determining the proximity of the tool to the NURBS surface; and controlling the at least one drive unit of the robot by resisting movement of the tool in response to the determined proximity to the NURBS surface.

Preferably, the NURBS surface is tessellated in determining the proximity of the tool thereto.

More preferably, the NURBS surface is coarsely tessellated and a first search is performed to identify a surface point close to a tool point of the tool, thereby enabling a first determination of the proximity of the tool to the NURBS surface.

Yet more preferably, an iterative procedure is employed to determine, from the identified surface point, a surface point having a minimum distance from the tool point.

In a preferred embodiment the iterative procedure is a Newton-Raphson iterative procedure.

According to another aspect of the present invention there is also provided a method of controlling an active-constraint robot, comprising the steps of: providing an active-constraint robot including a tool for operating on an element and at least one drive unit for controlling movement of the tool; providing a model including a NURBS surface describing at least one surface of the element to be operated on by the tool; determining the imaginary point of intersection of the axis of the tool and the NURBS surface; and controlling the at least one drive unit of the robot by resisting movement of the tool in response to the determined point of intersection.

Preferably, the NURBS surface is tessellated in determining the point of intersection.

More preferably, tessellations of a first resolution and at least one higher, second resolution are generated, the tessellations of the first resolution enabling a first determination of the point of intersection and the tessellations of the second resolution enabling a second, more accurate determination of the point of intersection.

According to a further aspect of the invention, there is provided a method of controlling an active-constraint robot, comprising:

providing an active-constraint robot (4) including a tool (14) for operating on element, and a drive unit (20,28, 38) for controlling movement of the tool;

providing a model including a NURBS surface describing a constraint surface associated with the element;

determining the imaginary point (I) of intersection of a force vector (V) representative of a force applied by a user to the tool and the NURBS surface; and controlling the drive unit (20,28,38) by resisting movement of the tool according to the determined point of intersection.

According to another aspect there is provided a method of controlling an active-constraint robot, comprising:

providing an active-constraint robot (4) including a tool (14) for operating on element, and a drive unit (20,28, 38) for controlling movement of the tool;

providing a model including a model surface describing a constraint surface associated with the element;

determining the imaginary point (I) of intersection of a force vector (V) representative of a force applied by a user to the tool and the model surface; and controlling the drive unit (20,28,38) by resisting movement of the tool according to the determined point of intersection.

According to another aspect there is provided an active-constraint robot (4) including:

a tool (14) for operating on an element;

a drive unit (20,28,38) for controlling movement of the tool;

means for holding a model including a NURBS surface describing a constraint surface associated with the element;

means for determining the imaginary point (I) of intersection of a force vector (V) representative of a force applied by a user to the tool and the NURBS surface; and a control for controlling the drive unit (20,28,38) by resisting movement of the tool according to the determined point of intersection.

According to another aspect there is provided an active-constraint robot (4) including:

a tool (14) for operating on an element and a drive unit (20,28,38) for controlling movement of the tool;

means for holding a model including a model surface describing a constraint surface associated with the element;

means for determining the imaginary point (I) of intersection of a force vector (V) representative of a force applied by a user to the tool and the model surface; and a control for controlling the drive unit (20,28,38) by resisting movement of the tool according to the determined point of intersection.

According to another aspect there is provided a method of controlling an active-constraint robot, comprising:

providing an active constraint robot (4) including a tool (14) for operating on an element, and a drive unit (20,28,38) for controlling movement of the tool;

providing a model describing a constraint surface associated with the element; and controlling the drive unit by resisting movement of the tool in a direction tangential to an adjacent constraint surface in dependence upon the shape of the constraint surface in a region surrounding the position of the tool.

According to another aspect there is provided An active constraint robot (4) including:
- a tool (14) for operating on an element;
- a drive unit (20,28,38) for controlling movement of the tool;
- means for holding a model describing a constraint surface associated with the element; and
- control means for controlling the drive unit by resisting movement of the tool in a direction tangential to an adjacent constraint surface in dependence upon the shape of the constraint surface in a region surrounding the position of the tool.

BRIEF DESCRIPTION OF THE DRAWINGS

The invention may be carried into practice in a number of ways and one specific robot system, along with various methods of controlling it, will now be described, by way of example, with reference to the accompanying drawings, in which.

DETAILED DESCRIPTION OF THE INVENTION

Figure 1:
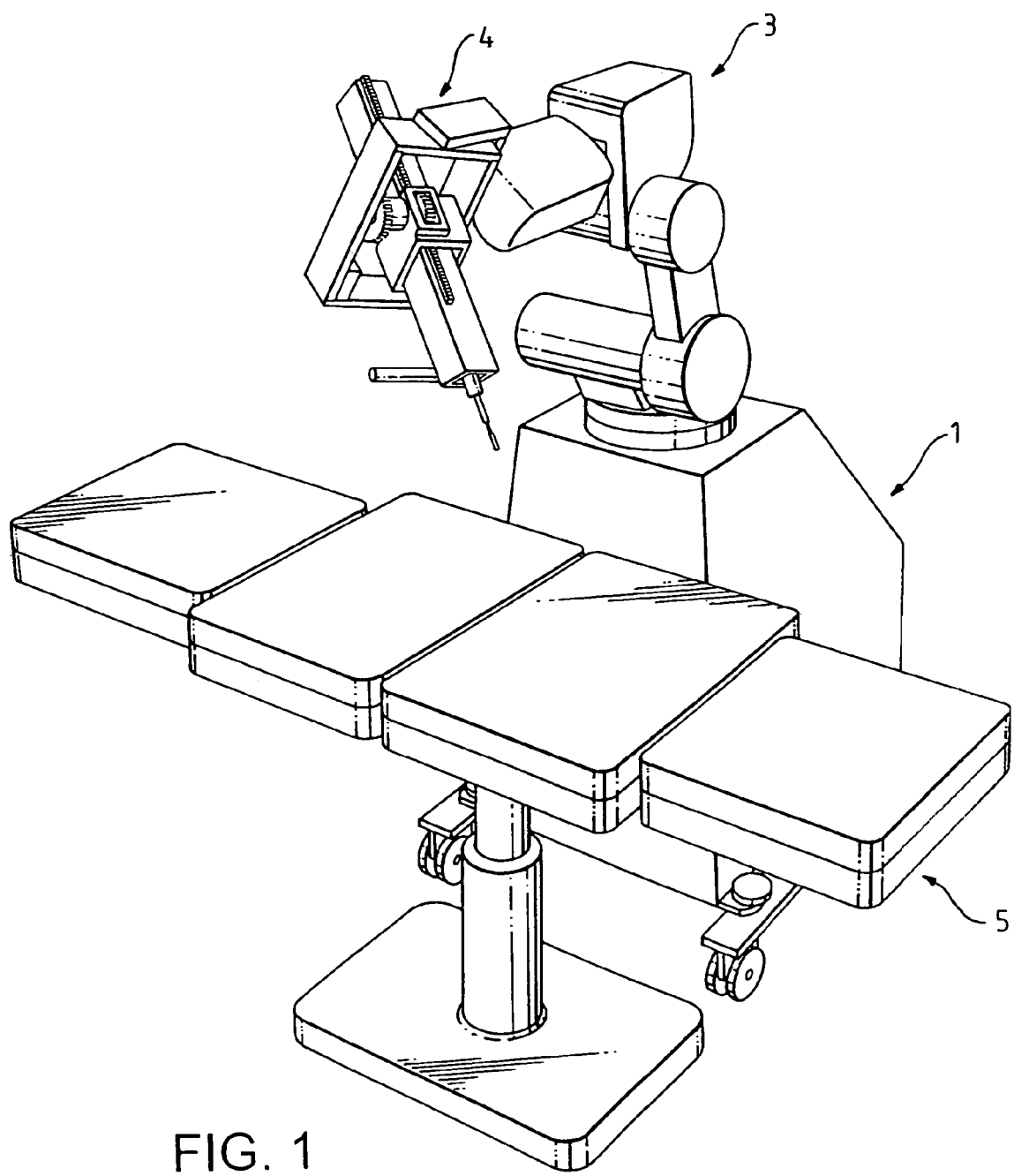
FIG. 1 illustrates generally a surgical robot system in accordance with a preferred embodiment of the present invention.
Figure 2:
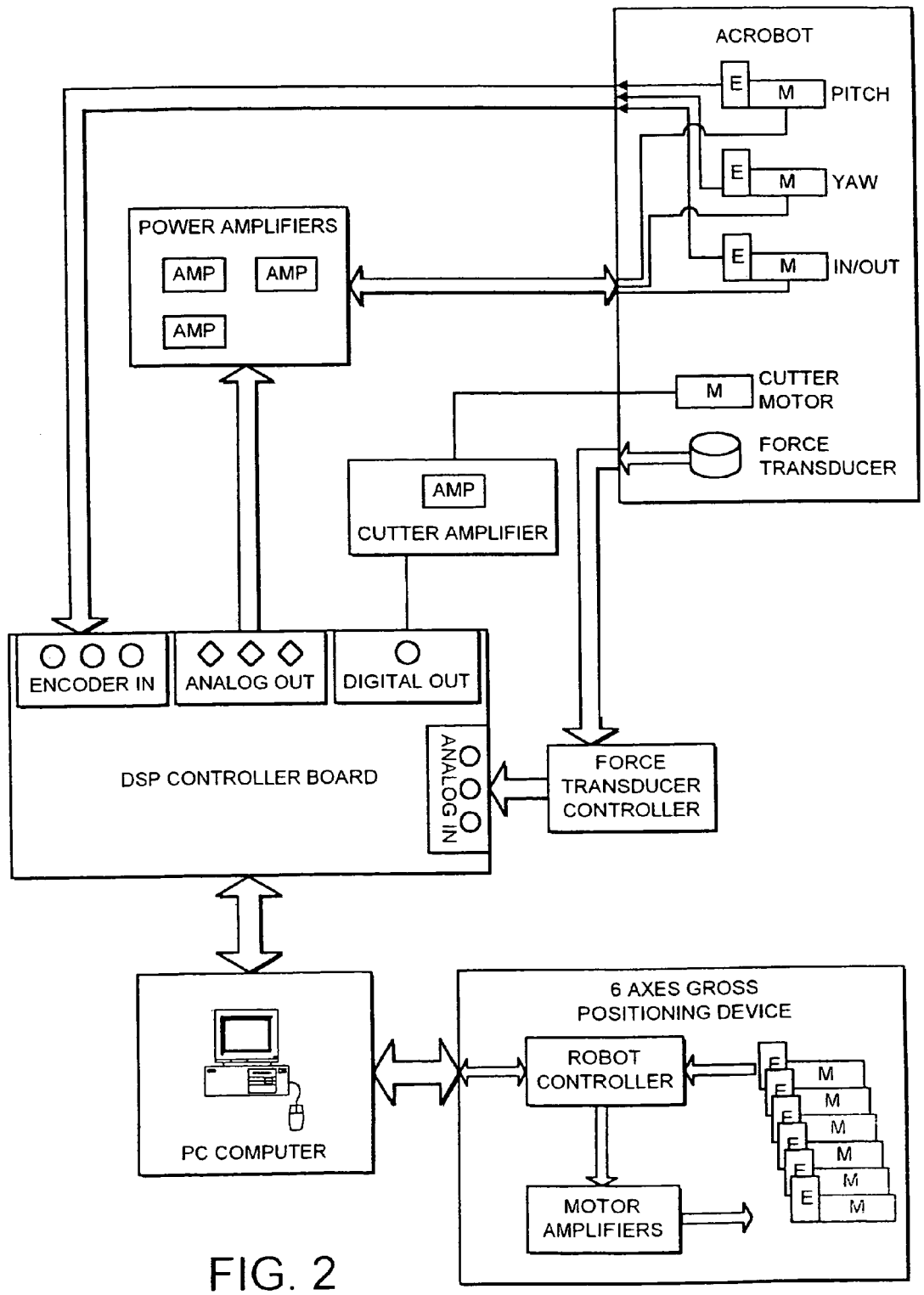
FIG. 2 is an electrical connection diagram for the robot system of FIG. 1.

FIGS. 1 to 2 illustrate generally a surgical robot system in accordance with a preferred embodiment of the present invention.

The surgical robot system comprises a trolley 1, a gross positioner 3, in this embodiment a six-axis gross positioner, mounted to the trolley 1, an active-constraint robot 4 coupled to the gross positioner 3, and a control unit. The robot 4 is of smaller size than the gross positioner 3 and actively controllable by a surgeon within a virtual region of constraint under the control of the control unit.

The trolley 1 provides a means of moving the robot system relative to an operating table 5. The trolley 1 includes two sets of clamps, one for fixing the trolley 1 to the floor and the other for clamping to the operating table 5. In this way, the robot system and the operating table 5 are coupled as one rigid structure. Also, in the event of an emergency, the trolley 1 can be unclamped and easily removed from the operating table 5 to provide access to the patient by surgical staff.

The gross positioner 3 is configured to position the robot 4, which is mounted to the tip thereof, in an optimal position and orientation in the region where the cutting procedure is to be performed. In use, when the robot 4 is in position, the gross positioner 3 is locked off and the power disconnected. In this way, a high system safety is achieved, as the robot 4 is only powered as a sub-system during the cutting procedure. If the robot 4 has to be re-positioned during the surgical procedure, the gross positioner 3 is unlocked, re-positioned in the new position and locked off again. The structure of the control unit is designed such as to avoid unwanted movement of the gross positioner 3 during the power-on/power-off and locking/releasing processes.

The operating table 5 includes a leg fixture assembly for holding the femur and the tibia of the leg of a patient in a fixed position relative to the robot 4 during the registration and cutting procedures. The leg of the patient is immobilised in a flexed position after the knee is exposed. The leg fixture assembly comprises a base plate, an ankle boot, an ankle mounting plate, a knee clamp frame and two knee clamps, one for the tibia and the other for the femur. The base plate, which is covered with a sterile sheet, is clamped to the operating table 5 and acts as a rigid support onto which the hip of the patient is strapped. The ankle is located in the ankle boot and firmly strapped with Velcro™ fasteners. The ankle mounting plate, which is sterilised, is clamped through the sterile sheet onto the base plate. The ankle boot is then located in guides on the ankle mounting plate. In this way, both the hip and the ankle are immobilised, preventing movement of the proximal femur and the distal tibia. The knee clamp frame is mounted to the operating table 5 and provides a rigid structure around the knee. The knee clamps are placed directly onto the exposed parts of the distal femur and the proximal tibia. The knee clamps are then fixed onto the knee clamp frame, thus immobilising the knee.

The robot 4 is a special-purpose surgical robot, designed specifically for surgical use. In contrast to industrial robots, where large workspace, high motion speed and power are highly desirable, these features are not needed in a surgical application. Indeed, such features are considered undesirable in introducing safety issues.

Figure 3:
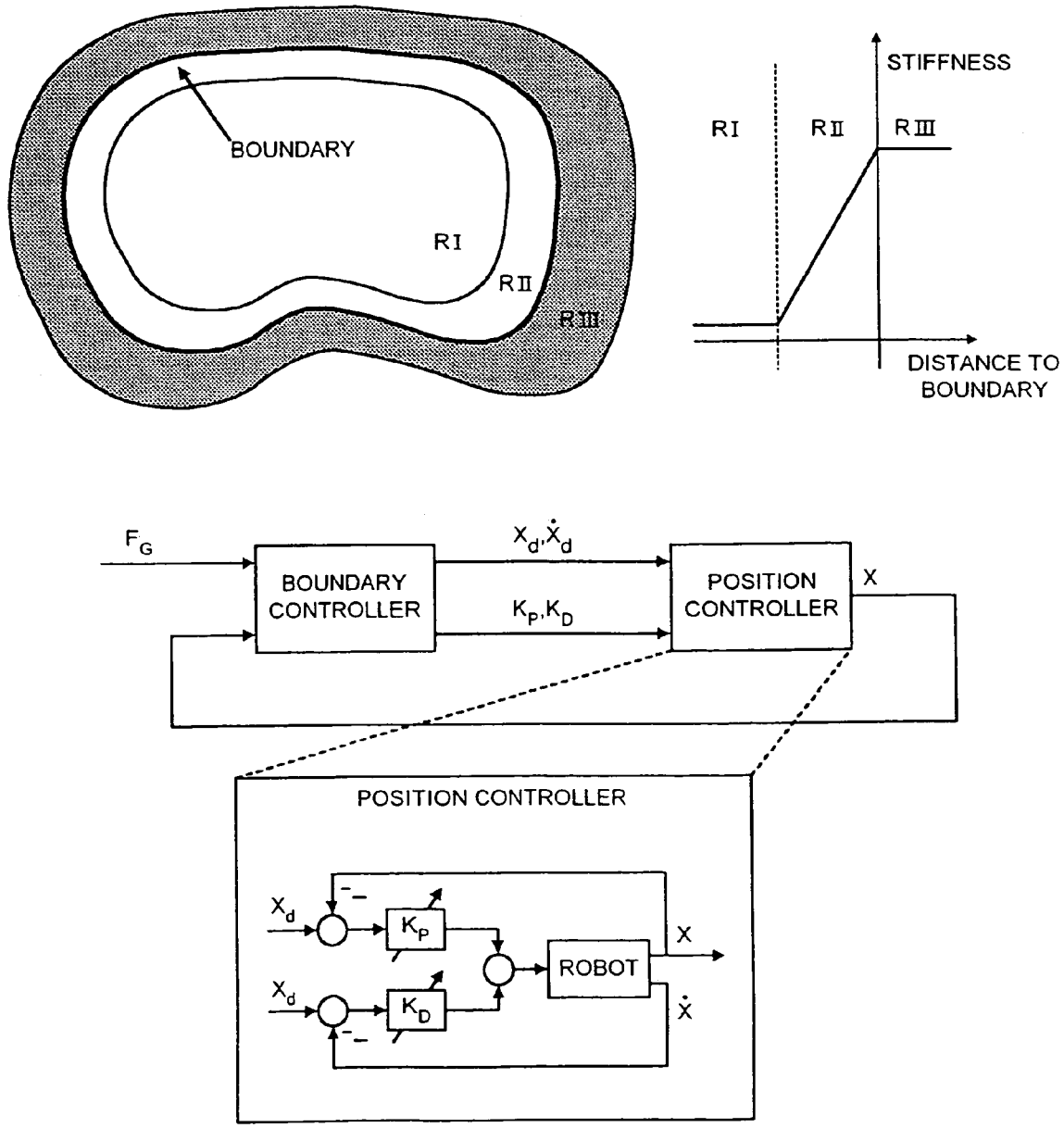
FIG. 3 explains the active constraint control principle.
Figure 4:
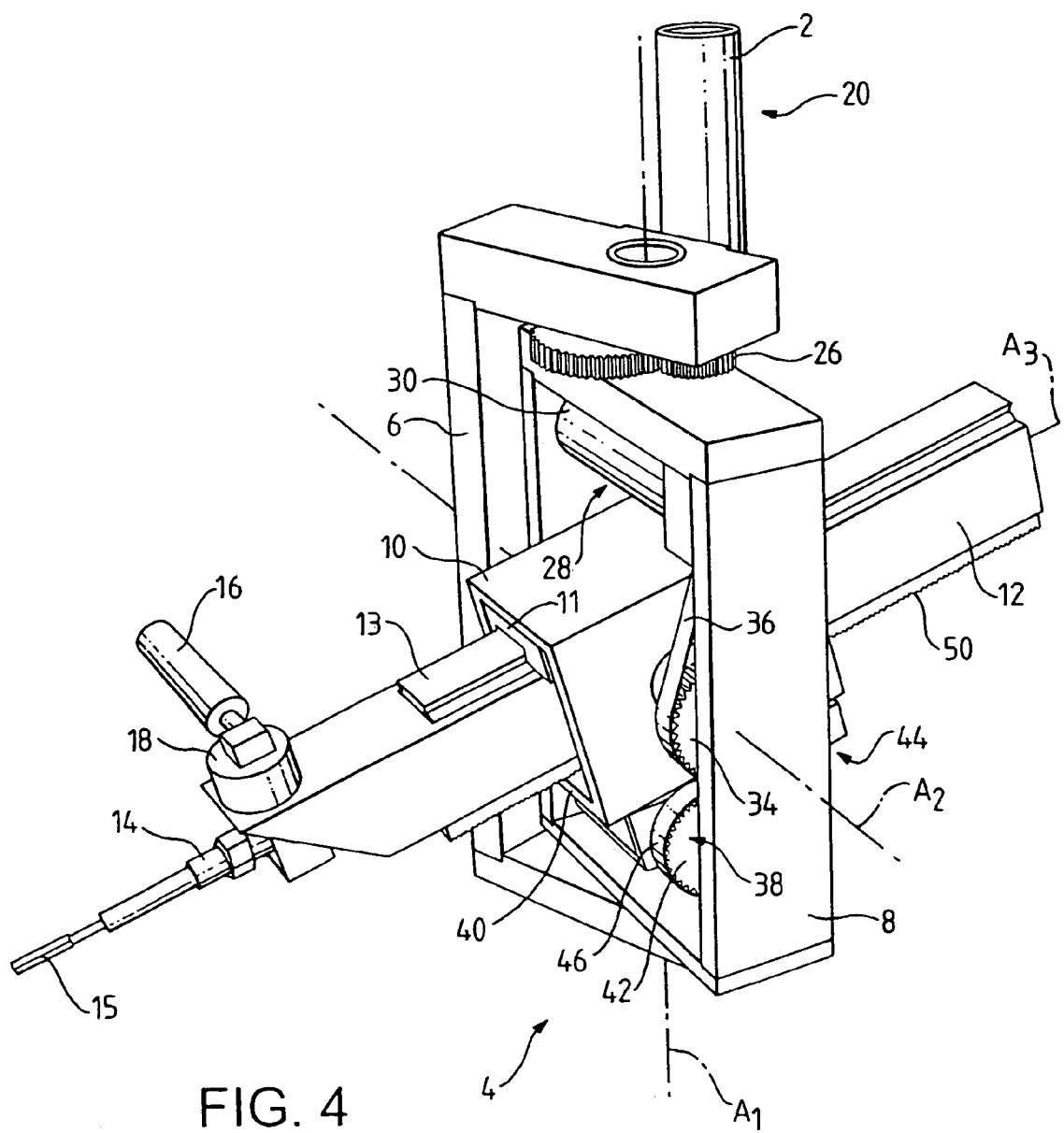
FIGS. 4 to 15 show various aspects of a preferred robot, for use with the robot system of FIG. 1.
Figure 5:
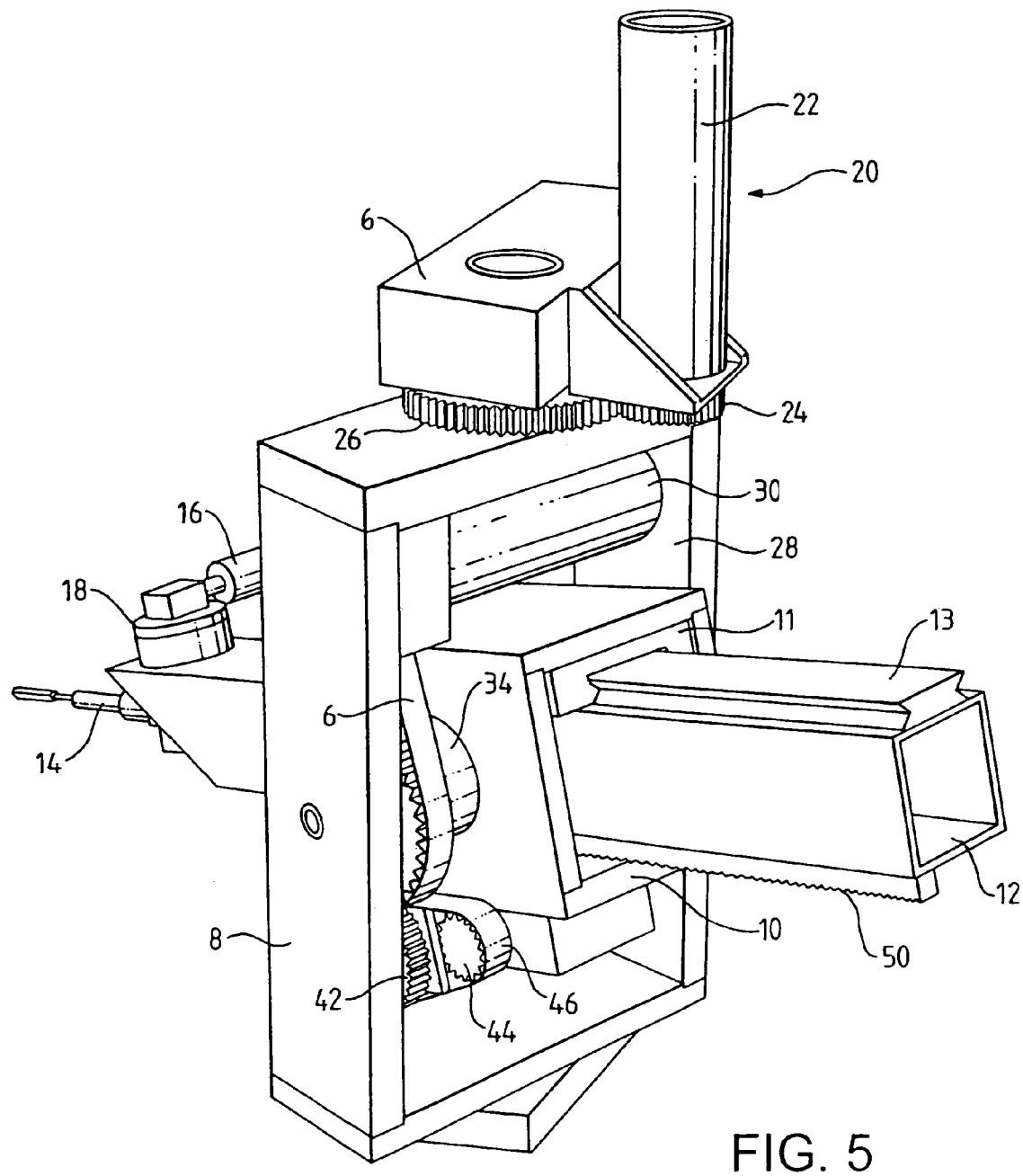
Figure 6:
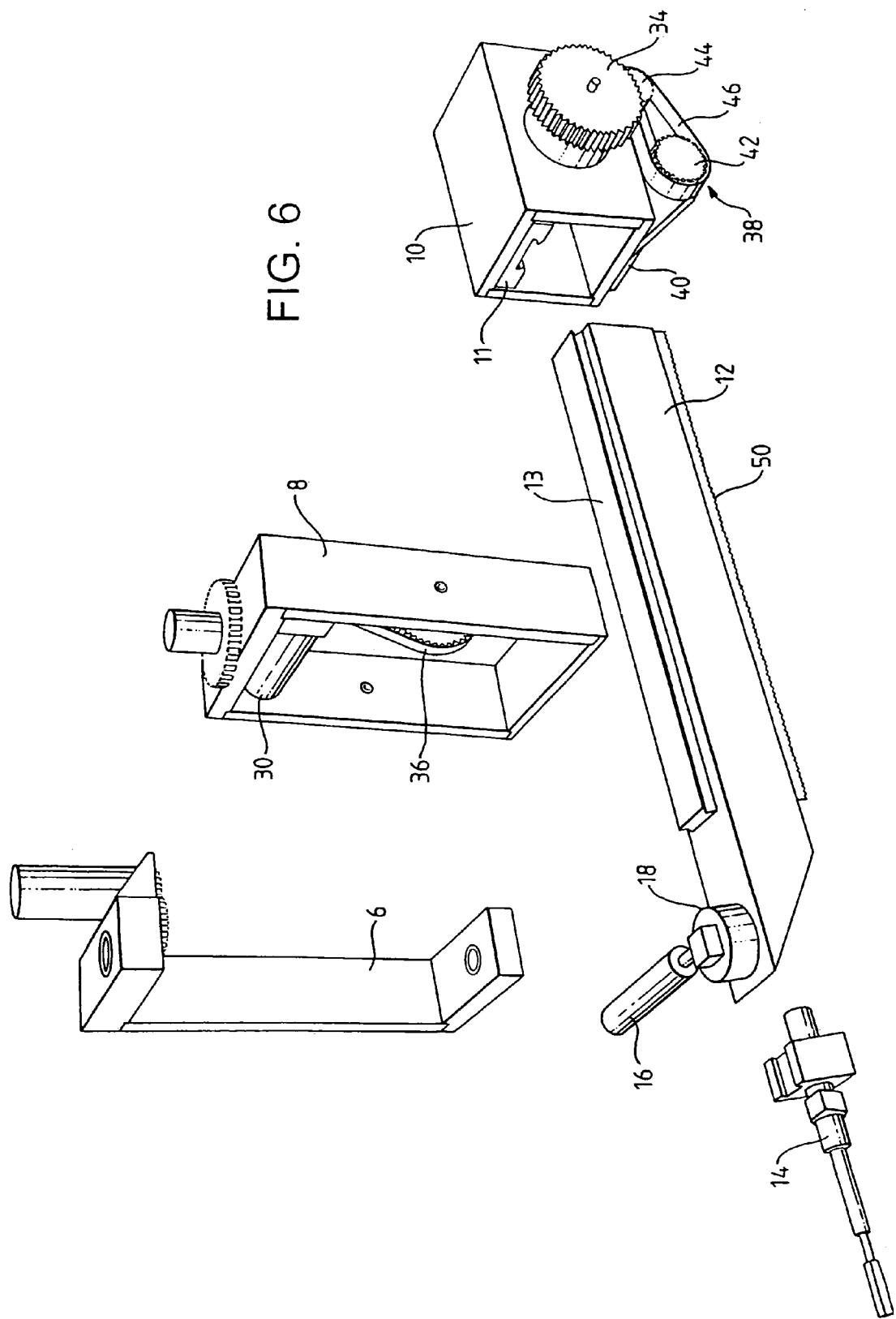
Figure 7:
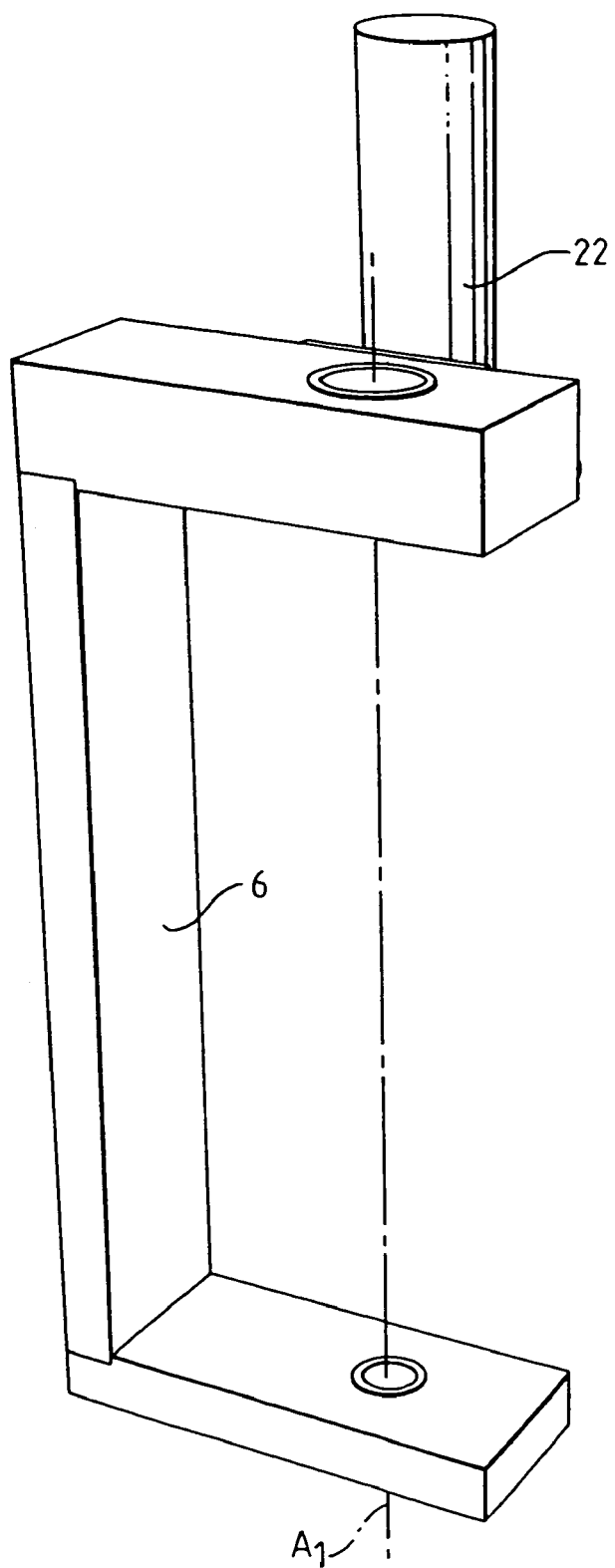
Figure 8:
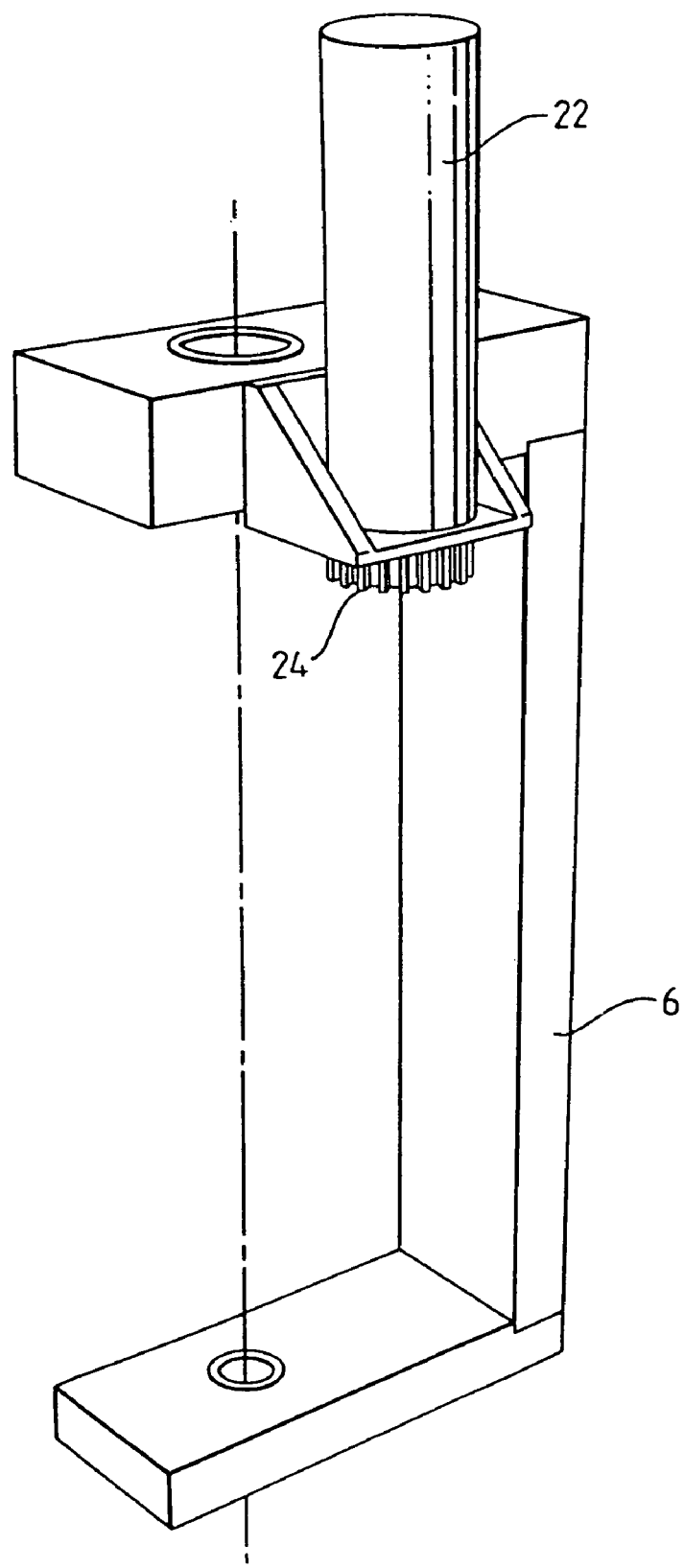
Figure 9:
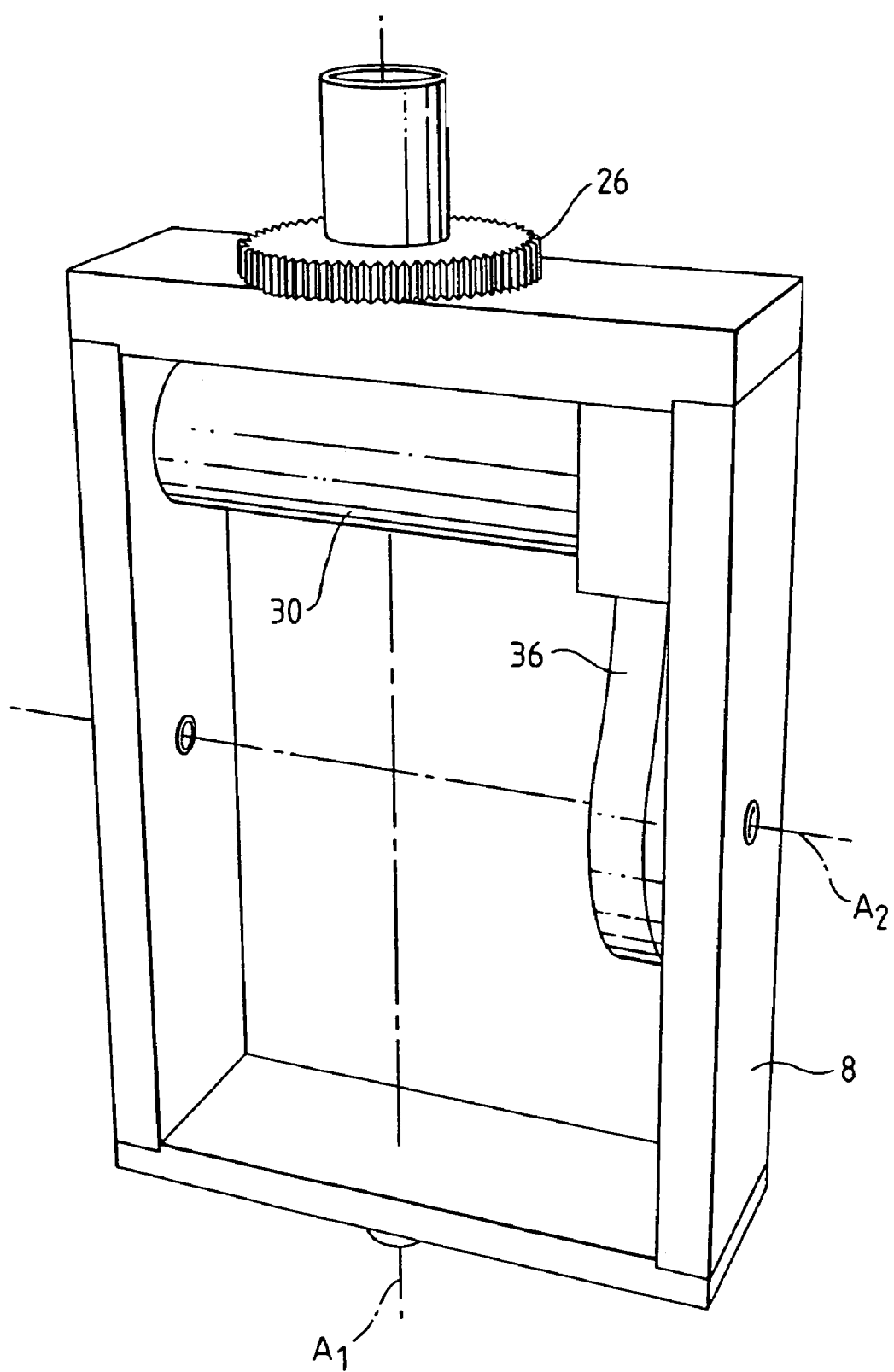
Figure 10:
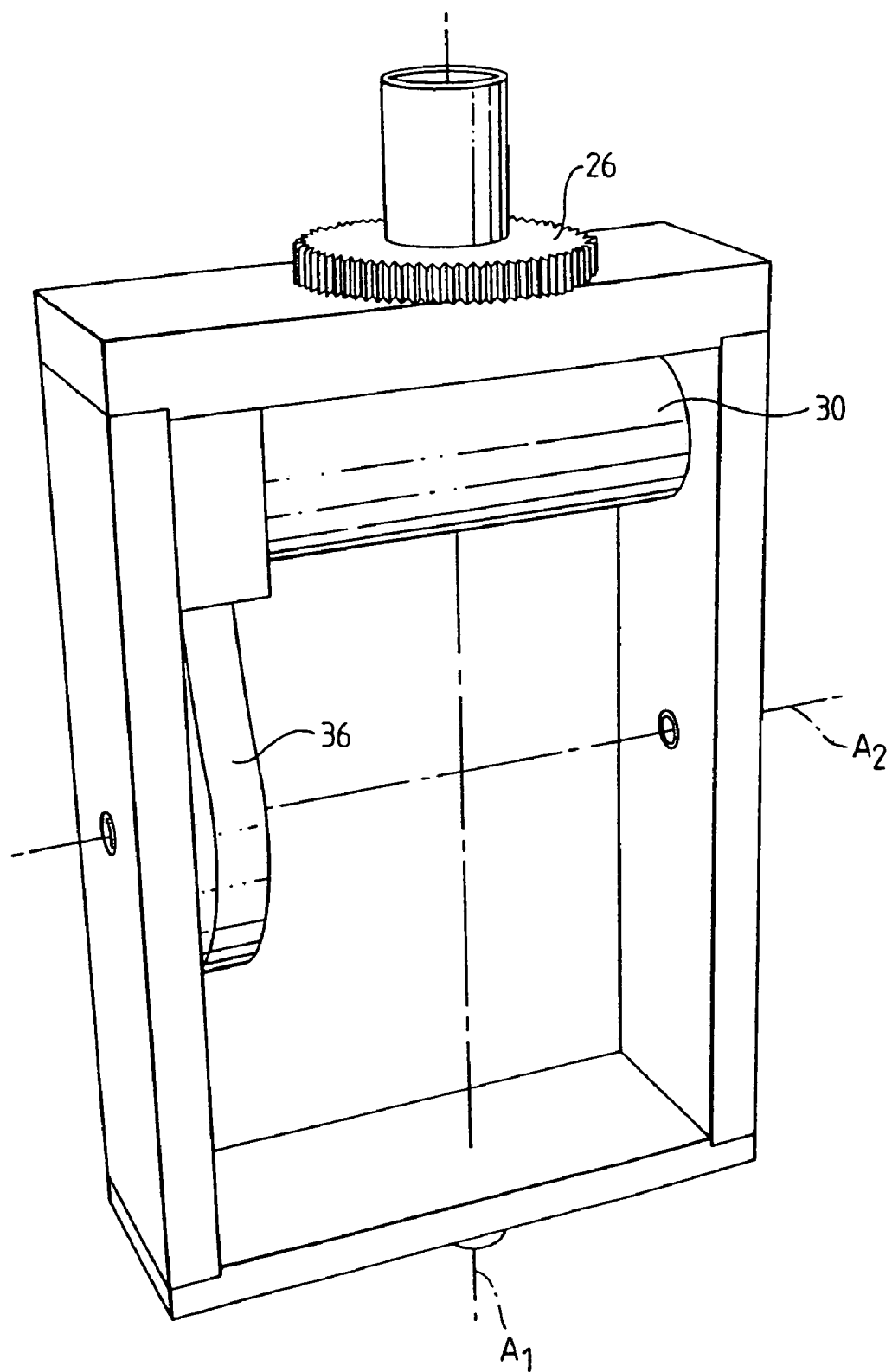
Figure 11:
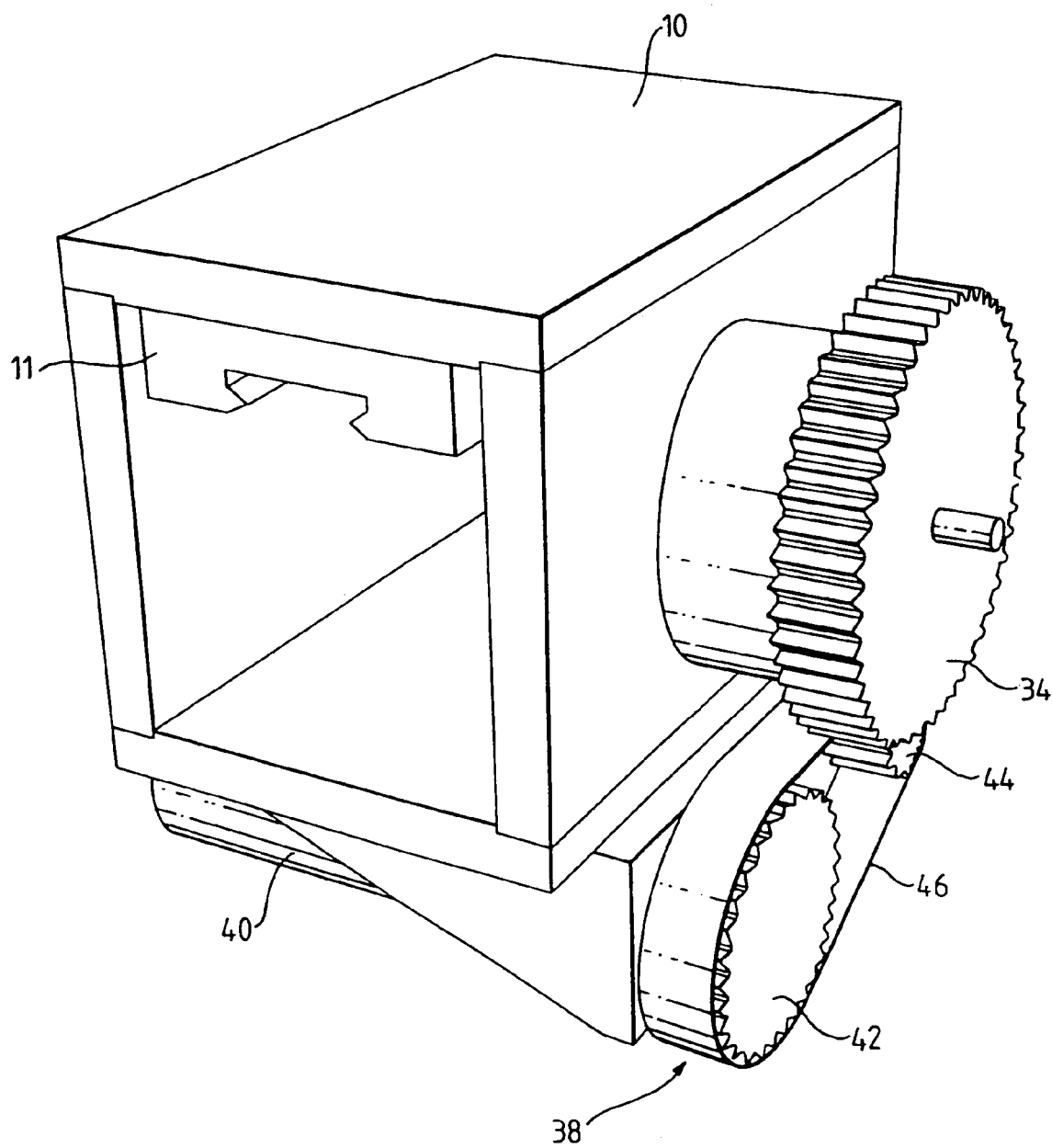
Figure 12:
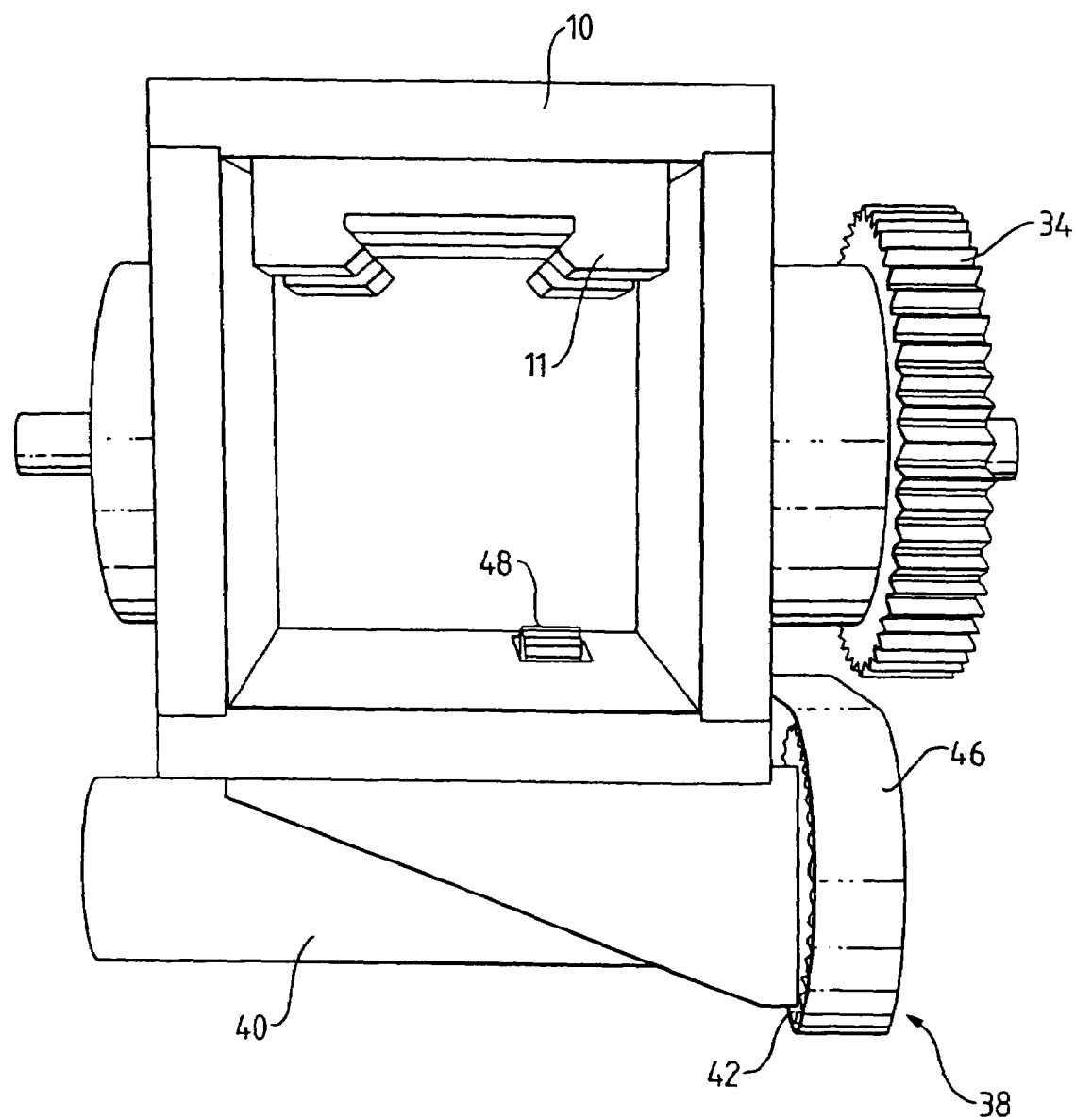
Figure 13:
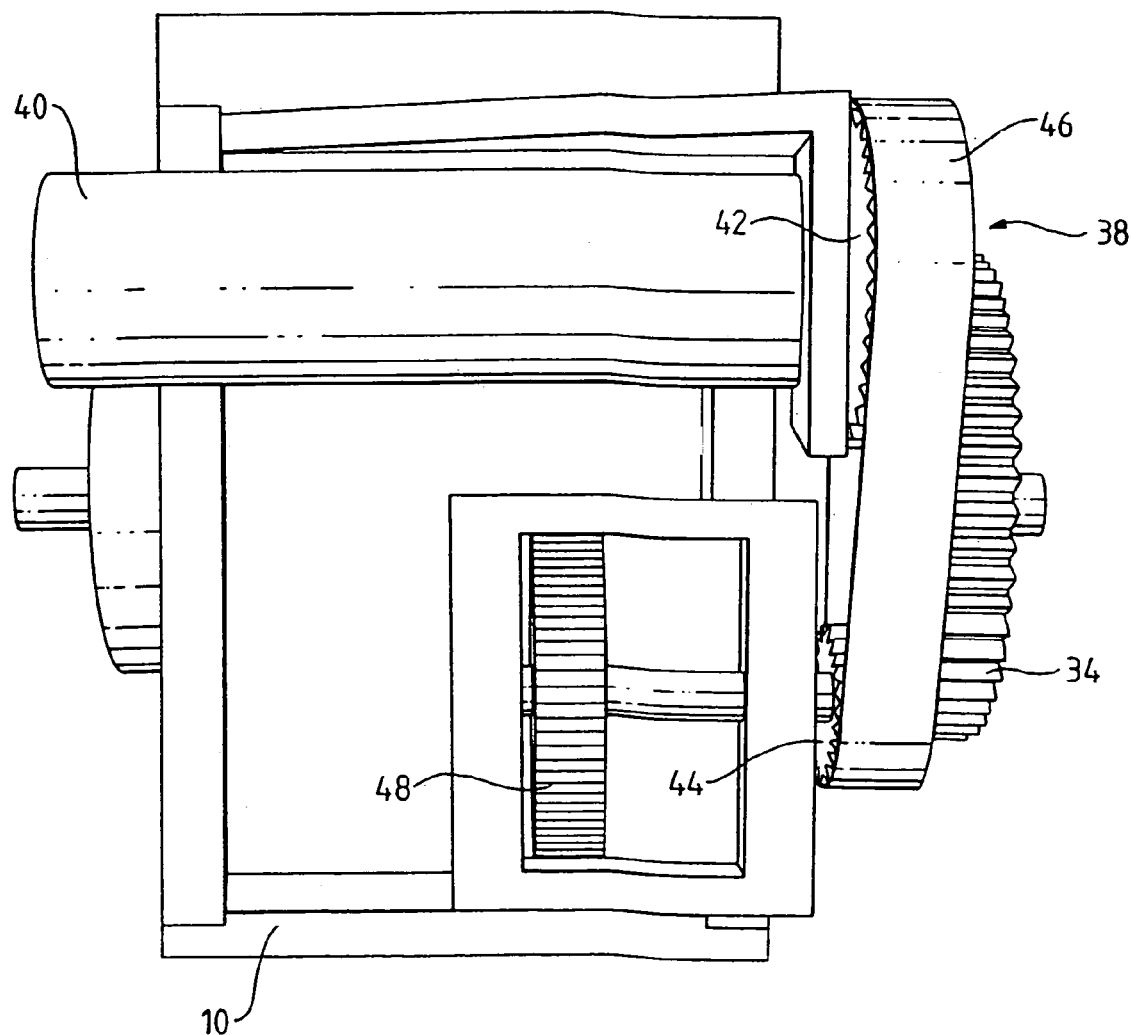
Figure 14:
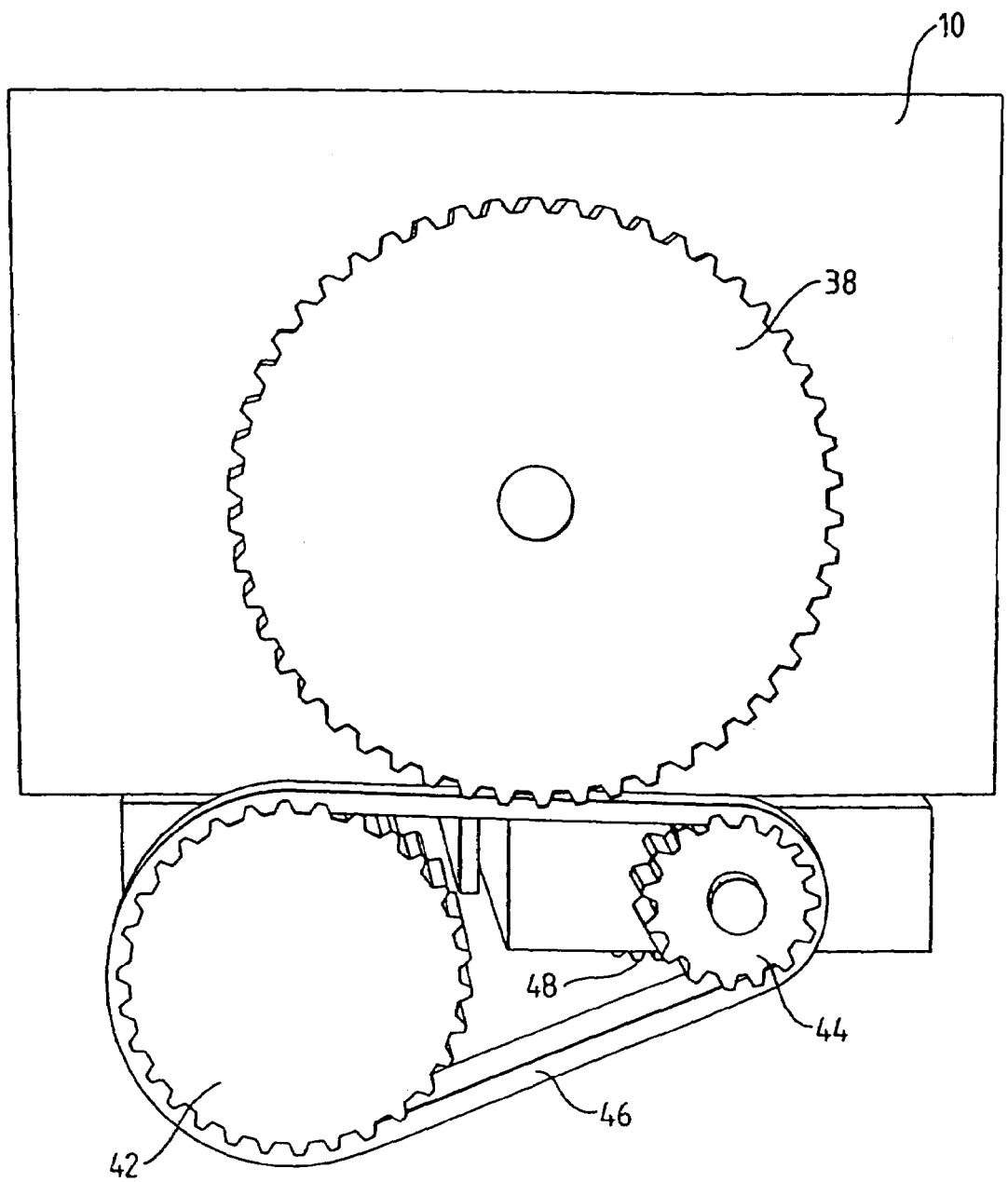
Figure 15:
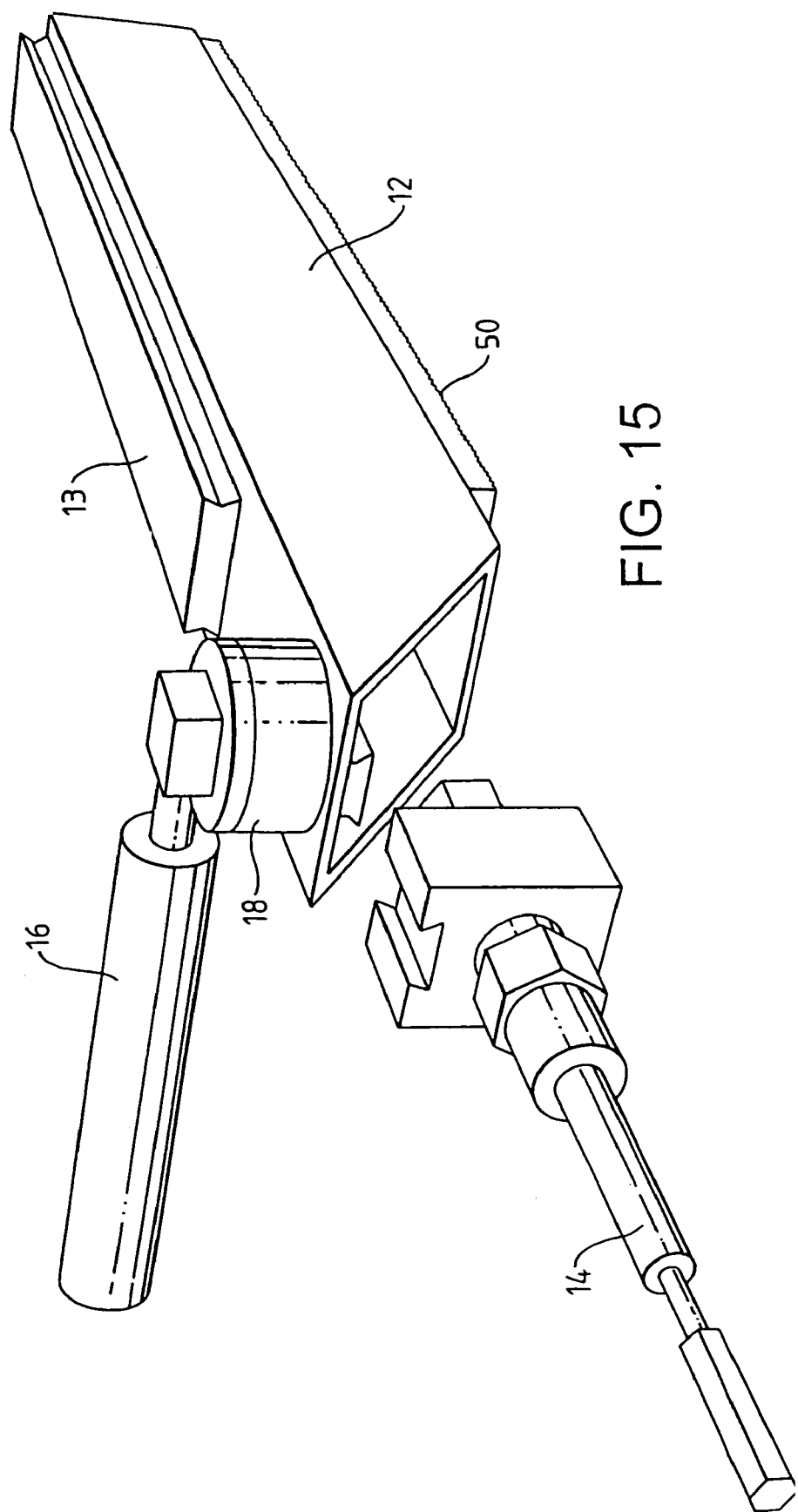

FIG. 3 shows in more detail a preferred implementation of the active constraint principle.

The inner loop is an independent joint position/velocity control loop. The position controller implements a PD control law in joint space:

$$\tau = K_P(\Theta_d - \Theta) + K_D(\dot{\Theta}_d - \dot{\Theta}) \quad (1)$$

$\tau$ is the torque output from the position controller to the robot motors. Position control gains $K_P$ (proportional) and $K_D$ (derivative) can be adjusted by the boundary controller to achieve the desired stiffness and damping of the robot. $\Theta_d$ and $\dot{\Theta}_d$ are joint position and velocity demands respectively and are set by the boundary controller. $\Theta$ and $\dot{\Theta}$ are actual joint position and velocity respectively (measured with encoders).

The boundary controller in the main control loop monitors the Cartesian position X of the cutter relative to the boundary of the safe region. It changes the gains of the position controller, and sets the position demand according to the minimum distance between the cutter and the boundary. The surgeon's motion commands are provided by measuring the surgeon's guiding force $F_G$. The Cartesian velocity demand for the position controller is set according to the surgeon's force:

$$\dot{X}_d = A \cdot F_G \quad (2)$$

A is the admittance, which again depends on the minimum distance to the boundary. The Cartesian position demands are transformed to joint space by inverse kinematics and inverse Jacobian computation [Sciavicco, L and Siciliano, B 1996. *Modelling and Control of Robot Manipulators*. McGraw-Hill]. The robot's workspace is divided into three regions, where the behaviour of the boundary controller is different. Region I (RI) is a region far from the boundary where the motion of the robot is free. The position control gains are low which means that the stiffness and damping of the robot is low. The admittance is high to achieve high sensitivity to the surgeon's commands, leading to smooth motion with a low guiding force. Position demand is set to the current position.

Region II (RII) is an area near the boundary. The boundary controller increases the position control gains and decreases the admittance as the minimum distance between the cutter and the boundary decreases. This makes the robot stiffer when the cutter approaches the boundary. Admittance at the boundary is set to 0, effectively transforming the whole controller into a position controller with high gains. Position demand is again set to the current position.

Region III (RIII) is a region beyond the boundary and is outside the safe region and so must never be reached. However, this is impossible to achieve without very large and powerful motors. Instead, the position control gains are set to very high values, with the position demand set to the nearest point on the boundary in order to push the cutter back into the safe region. In this way a stable control without vibrations is achieved at the boundary, since the constraining force increases gradually over the Region II. If that was not the case (no Region II), it would be easy to push the cutter into Region III (due to the delays in the control loop), leading to a very high resisting force. This would push the cutter back inside the boundary and, since there is no resisting force in Region I, the process could be repeated, resulting in the cutter vibrating at the boundary.

The boundary control is very computationally expensive, due to the sophisticated algorithms for adjusting the gains and demands for the position controller, and kinematics computations. The time delay between two subsequent computations can cause stability problems. The independent joint position/velocity control incorporates a very simple control law and can therefore be executed at a higher sample rate, which increases stability of the boundary control.

FIGS. 4 to 15 illustrate an active-constraint robot 4 in accordance with a preferred embodiment of this aspect of the present invention.

The robot 4 is of a small, compact and lightweight design and comprises a first body member 6, in this embodiment a C-shaped member, which is fixedly mounted to the gross positioner 3, a second body member 8, in this embodiment a rectangular member, which is rotatably disposed to and within the first body member 6 about a first axis $A_1$, a third body member 10, in this embodiment a square tubular member, which includes a linear bearing 11 mounted to the inner, upper surface thereof and is rotatably disposed to and within the second body member 8 about a second axis $A_2$ substantially orthogonal to the first axis $A_1$, a fourth body member 12, in this embodiment an elongate rigid tubular section, which includes a rail 13 which is mounted along the upper, outer surface thereof and is a sliding fit in the linear bearing 11 on the third body member 10 such that the fourth body member 12 is slideably disposed to and within the third body member 10 along a third axis $A_3$ substantially orthogonal to the second axis $A_2$, and a cutting tool 14 which is removably disposed to the forward end of the fourth body member 12.

In this embodiment the axes of the two rotational joints, that is, the pitch and yaw, and the translational joint, that is the in/out extension, intersect in the centre of the robot 4, thus forming a spherical manipulator.

In this embodiment the cutting tool 14 includes a rotary cutter 15, for example a rotary dissecting cutter, at the distal end thereof.

In this embodiment the fourth body member 12 is hollow to allow the motor, either electric or air-driven, and the associated cabling or tubing of the cutting tool 14 to be located therewithin.

The robot 4 further comprises a grip member 16, in this embodiment a handle, which is coupled to the fourth body member 12 and gripped by a surgeon to move the cutting tool 14, and a force sensor unit 18, in this embodiment a force transducer, for sensing the direction and magnitude of the force applied to the grip member 16 by the surgeon. In use, the surgeon operates the robot 4 by applying a force to the grip member 16. The applied force is measured through the force sensor unit 18, which measured force is used by the control unit to operate the motors 22, 30, 40 to assist or resist the movement of the robot 4 by the surgeon.

The robot 4 further comprises a first back-driveable drive mechanism 20, in this embodiment comprising a servo-controlled motor 22, a first gear 24 connected to the motor 22 and a second gear 26 connected to the second body member 8 and coupled to the first gear 24, for controlling the relative movement (yaw) of the first and second body members 6, 8.

The robot 4 further comprises a second back-driveable drive mechanism 28, in this embodiment comprising a servo-controlled motor 30, a first toothed pulley 32 connected to the motor 30, a second toothed pulley 34 connected to the third body member 10 and a belt 36 coupling the first and second pulleys 32, 34, for controlling the relative movement (pitch) of the second and third body members 8, 10.

The robot 4 further comprises a third back-driveable drive mechanism 38, in this embodiment comprising a servo-controlled motor 40, a first toothed pulley 42 connected to the motor 40, a second toothed pulley 44 rotatably mounted to the third body member 10, a belt 46 coupling the first and second pulleys 42, 44, a pinion 48 connected to the second pulley 44 so as to be rotatable therewith and a rack 50 mounted along the lower, outer surface of the fourth body member 12 and coupled to the pinion 48, for controlling the relative movement (in/out extension) of the third and fourth body members 10, 12.

In this embodiment the rotational axes, that is, the pitch and yaw, of the robot 4 are in the range of about ±30°, and the range of extension is about from 20 to 35 cm. The permitted workspace of the robot 4 is constrained to a relatively small volume in order to increase the safety of the system.

In a preferred embodiment the power of the motors 22, 30, 40 is relatively small, typically with a maximum possible force of approximately 80 N at the tip of the robot 4, as a further safety measure.

In this embodiment all three of the joints between the first to fourth body members 6, 8, 10, 12 are back-driveable and have similar mechanical impedance. With this configuration, the cutting tool 14 at the tip of the robot 4 can easily be moved with a low force in any direction when the motors 22, 30, 40 are unpowered. This is a significant feature of the robot 4 as the surgeon, when guiding the robot 4, is able to feel the contact forces at the cutter 15, which would be undetectable when using a very rigid and non-back-driveable robot.

During a surgical procedure, the robot system is covered by sterile drapes to achieve the necessary sterility of the system. This system advantageously requires only the sterilisation of the cutting tool 14 and the registration tool as components which are detachably mounted to the fourth body member 12 of the robot 4. After the robot system is so draped the registration-tool and the cutting tool 14 can be pushed through the drapes and fixed in position.

We now turn to a consideration of some NURBS-based methods of controlling an active constraint robot. NURBS stands for Non-Uniform Rational B-Splines.

Where flat surfaces are used, for example, with the current generation of total-knee prosthesis components, and simple, typically spherical, geometry exists for unicompartmental components, control can be based on simple geometrical primitives. In the case of a NURBS-based approach, however, no basic primitives are available, and a control methodology has to be used to restrict the movements of the surgeon to comply with the surface or surfaces as defined by the NURBS control points.

In the ACROBOT™ robot system as described above, a cutter tool is positioned at the end of a robot arm. This arm is configured to provide yaw, pitch and in/out motions for the cutter tool. Each of these motions is driven by a motor, with the motors being geared to be back-driveable, that is, moveable under manual control when the motors are unpowered. With the motors powered, the robot is capable of aiding the surgeon, for example, by power assisting the movements, compensating for gravity, or resisting the movements of the surgeon, normally at a constraint boundary to prevent too much bone from being cut away or damage to the surrounding tissue. Assistance or resistance is achieved by sensing the applied force direction and applying power to the motors in a combination which is such as to produce force either along that force vector for assistance, or backwards along that force vector for resistance.

One approach to control is to use a simple proximity test, as will now be described.

In a simple system, a flat plane and an outline tunnel, which is defined by a series of co-ordinates around its outline, could define the constraint region, with the proximity to the plane being computed from the plane equation, and the proximity to the tunnel being computed by searching the co-ordinate list to find the nearest matching outline segment. With this control system, as the surgeon moves the cutter tool closer to a boundary, the robot would be stiffened and the resistance increased.

Figure 16A:
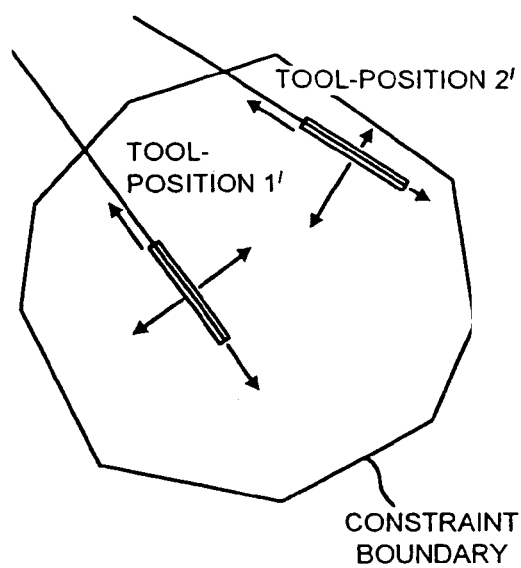
FIG. 16A illustrates a method of control using a proximity test.
Figure 16B:
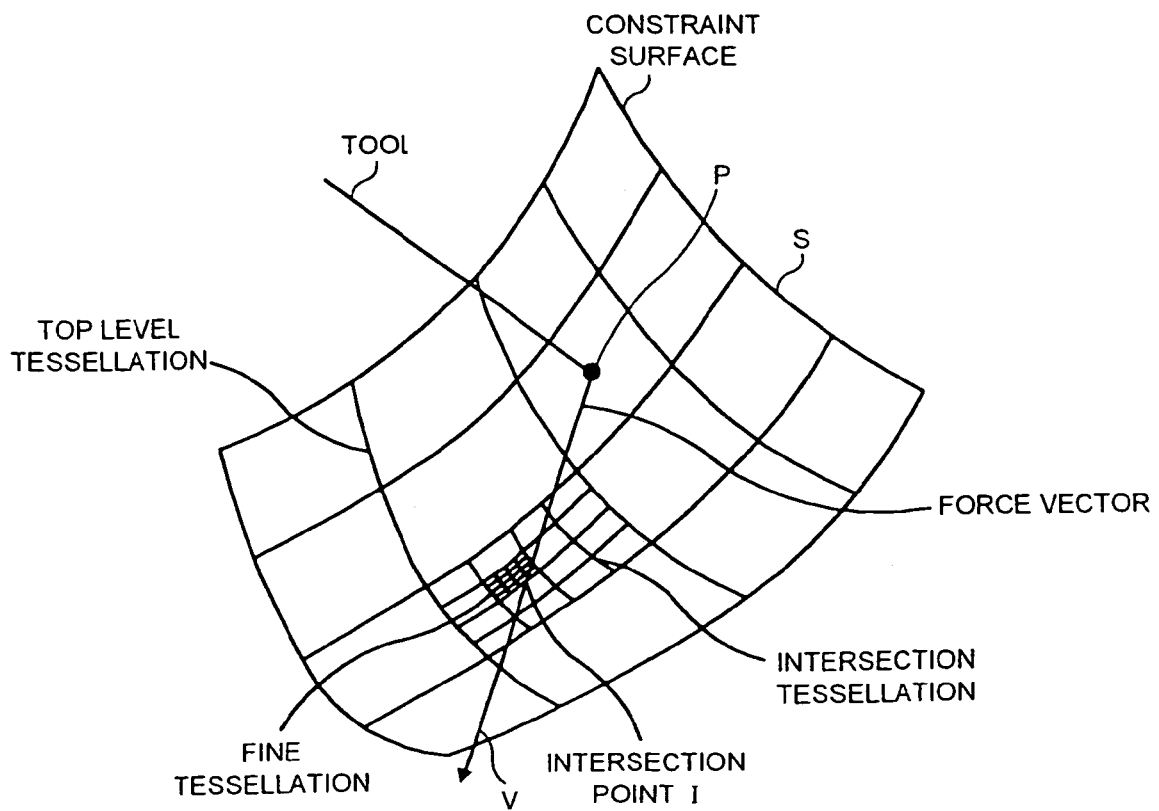
FIG. 16B illustrates a method of control using a surface-intersection test.

FIG. 16A illustrates the general principle of such a simple proximity test, being exemplified in 2D for ease of illustration. In position 1', the tool tip is well away from the constraint region, so the ease of movement (indicated by the lengths of the arrows) is free in all directions. In position 2', the tool is close to the boundary, so, whereas movement away from the boundary is easy, any movement towards the boundary is made difficult by the application of a constraining force pushing back against any outward motion.

Rather than measure absolute proximity, it is proposed in this aspect of the present invention to provide a more effective method of determination in which, for a given force vector, the movements of the surgeon are analysed to determine whether those movements would break through the constraint boundary, and the distance to that section of the boundary is determined, rather than merely finding the closest section. This control method advantageously allows the surgeon to work freely parallel, but close to, a surface boundary. If a simple proximity test were used, working parallel and close to a surface boundary would be difficult since the close boundary proximity would be detected, resulting in resistance from the robot.

A NURBS proximity determination has the advantage of being computationally less intensive than other NURBS computations. In order to determine the closest point on a NURBS surface S from a particular point P, a Newton-Raphson iterative approach is used [Piegl, L., Tiller W., '*The NURBS Book*'—*Second Edition, Springer Verlag*, 1997 (ISBN 3-540-61545-8)]. This iteration is set up to minimise the function S-P. The starting point for the search can theoretically be anywhere on the surface. However, faster convergence on the minimum can be achieved by first tessellating the NURBS surface coarsely into a set of quadrilaterals and then scanning the tessellated surface for the closest tessellation. The search is then started from the closest tessellation found. Once the closest point is found, the distance between this point and the tool tip is computed, and constraint forces are applied to the active-constraint robot to ensure that boundaries are not crossed.

An alternative approach to surface-proximity testing is surface-intersection testing, and that latter approach will now be described.

The determination of the intersection with the NURBS surface allows for a more accurate determination as to whether a restraining force needs to be applied near a constraint boundary. This determination allows for a differentiation between beading towards or away from a surface, in which cases constraint forces are required or not required respectively, whereas a simple proximity test does not allow for such a determination and would result in the application of a constraining force in all circumstances for safety. Collision detection with a NURBS surface is, however, a difficult task. It is simpler to tessellate the surface into small regions and scan these regions to determine the intersection point. However, there comes a point where this becomes time consuming, since, for a high resolution, to determine the intersection point exactly, a large number of small tessellated triangles will be needed. The search time for such a list would be considerable.

It has been established that it is possible, providing the surface is relatively smooth, to reduce the search time by hierarchically tessellating the surface. An initial low-resolution tessellated surface with relatively large facets is first tested to determine the approximate position of the intersection. When this position is found, the position indexes a higher resolution tessellated grid around this region. This grid is localised and therefore still of relatively small in size. Trade-offs between memory and processing power may allow deeper tessellated nesting to provide a higher resolution for the intersection point.

Figure 17:
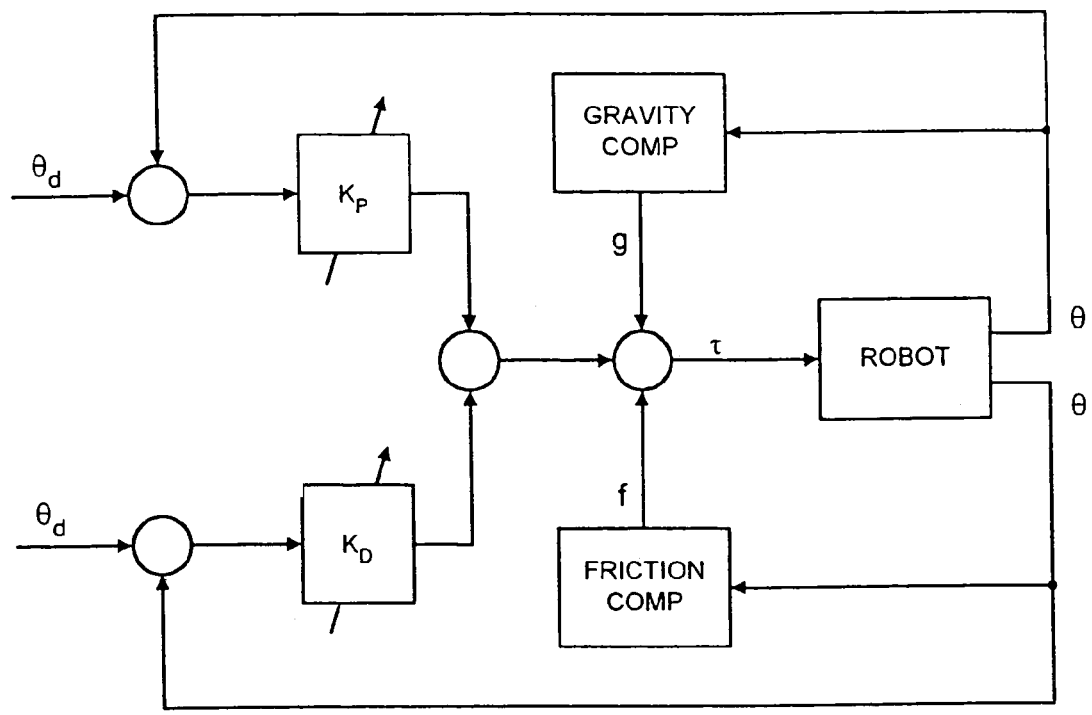
FIG. 17 shows a robot control scheme with PD control law and friction and gravity compensation.

FIG. 17 illustrates this determination graphically. The tool tip P is represented by a ball on the end of a shaft. For a complex surface, a ball-ended or acorn-type tool would be used rather than the barrel cutter used for flat plane cutting. A force vector V, indicating the direction in which the surgeon is applying force, is projected from the tool tip P through the NURBS surface S.

In a first pass, the closest large tessellation is found. This position is then linked to a finer tessellation mesh, and finally to a yet finer tessellation mesh. In this particular example, the intersection point I is found after a search through, at maximum, 48 facets. In an ordinary search without hierarchy, up to 4096 facets would have had to have been searched to find the intersection point I to the same resolution. It will be understood that this example is fairly simplistic in order to allow for easy exemplification of the concept. In reality, the sizes of the facets, and the number at each level will be governed by the complexity of the surface. A very simple smooth surface needs to contain few facets at any level of detail, whereas a more complex or bumpy surface will require more facets to provide an approximation of the bumps at the top level.

Once the intersection point I is found, the distance from the tool tip P is computed simply, and the force applied by the surgeon measured. The constraining force required is then a function of the distance and the force.

We now turn to a more detailed consideration of the control dynamics of active constraint. Three major problems of known active constraint controls for the ACROBOT are as follows:

1. Vibrating motion at an inclined plane boundary;
2. "Springiness" at the boundary; and
3. The difficulties of moving the tool along the boundary.

In order to design a more suitable boundary controller it is worth analysing the dynamic behaviour of the ACROBOT under active constraint control. The dynamic model of a general n-DOF (Degrees of Freedom) manipulator can be represented in a standard form as $$M(\Theta)\ddot{\Theta}+h(\Theta,\dot{\Theta})+f(\Theta,\dot{\Theta})+g(\Theta)=\tau+J^T(\Theta)F_E \quad (1)$$

where $\Theta$, $\dot{\Theta}$ and $\ddot{\Theta}$ are joint position, velocity and acceleration vectors (n×1) respectively. M is the inertia matrix (n×n) of the robot, which is symmetric and positive definite. h is a vector (n×1) of Coriolis and centrifugal torques—the joint torques caused by motion of other joints. $f$ and g are the joint friction vector (n×1) and the gravity vector (n×1) respectively. $\tau$ is the vector (n×1) of joint motor torques. $F_E$ is a generalised force vector (6×1) of the external forces and torques exerted at the tip of the manipulator. $J^T$ is the transpose of the Jacobian matrix of the robot, which transforms $F_E$ into joint space.

Equation (1) represents the dynamic model as a set of n second-order coupled and nonlinear differential equations.

1. Closed-Loop Dynamics

The robot control law can be designed as $$\tau=K_P(\Theta_d-\Theta)+K_D(\dot{\Theta}_d-\dot{\Theta})+f^*(\Theta,\dot{\Theta})+g^*(\Theta) \quad (2)$$

where $K_P$ and $K_D$ are diagonal proportional and derivative gain matrices respectively (n×n). $\Theta_d$ and $\dot{\Theta}_d$ are joint position and velocity demand vectors respectively (n×1). $f^*$ and $g^*$ are friction and gravity compensation vectors (n×1). This robot control scheme is shown in FIG. 17.

Substituting (2) into (1) yields $$M(\Theta)\ddot{\Theta}+K_D\dot{\Theta}+K_P\Theta+\delta=K_P\Theta_d+K_D\dot{\Theta}_d+J^T(\Theta)F_E \quad (3)$$

where $$\delta=h(\Theta,\dot{\Theta})+\Delta f(\Theta,\dot{\Theta})+\Delta g(\Theta)$$

$$\Delta f(\Theta,\dot{\Theta})=f(\Theta,\dot{\Theta})-f^*(\Theta,\dot{\Theta})$$

$$\Delta g(\Theta)=g(\Theta)-g^*(\Theta)$$

The contributions of $\Delta f$ and $\Delta g$ equal zero in the case of perfect compensation. In the real world, it is difficult to achieve that (especially for friction compensation). It is, however, possible to achieve relatively small $\Delta f$ and $\Delta g$. It can be observed, that the contribution of Coriolis and centrifugal torques h is small when the robot motion is slow. This is true in case of the ACROBOT—the robot is guided by a human operator, which is relatively slow. In view of this and for the sake of clarity of further analysis, the contribution of $\delta$ can be discarded. The dynamic behaviour of the robot is therefore governed mostly by inertia of the manipulator (M), control gains ($K_P$ and $K_D$), external force ($F_E$) and the choice of control demands ($\Theta_d$ and $\dot{\Theta}_d$).

It can be observed that in the case of high inertia of the system, the contribution of $F_E$ (i.e. human guiding force) is relatively small, and the motion of the robot depends mainly on the control parameters. In other words, the robot is non-backdriveable. It also has to be noted, that the motor inertia is included in M, which can be quite high, especially with small electrical motors with high gear ratios.

Further analysis will be performed for a single joint only, due to difficulties of analysing the full set of nonlinear differential equations. Equation 3 can be written (discarding $\delta$ and contributions of other joints) for a single joint as $$M\ddot{\Theta}+K_D\dot{\Theta}+K_P\Theta=K_P\Theta_d+K_D\dot{\Theta}_d+\tau_E \quad (4)$$

Where $\tau_E$ represents the portion of the external force affecting the joint (inline with the axis of the joint). The Laplace transform of Equation 4 yields $$Ms^2\Theta(s)+K_Ds\Theta(s)+K_P\Theta(s)=K_P\Theta_d(s)+K_D\dot{\Theta}_d(s)+\tau_E(s) \quad (5)$$

from which the transfer functions for each of the systems inputs can be derived:

$$C_P(s)=\frac{\Theta(s)}{\Theta_d(s)}=\frac{K_P}{Ms^2+K_Ds+K_P} \quad (6)$$

$$C_V(s)=\frac{\Theta(s)}{\dot{\Theta}_d(s)}=\frac{K_D}{Ms^2+K_Ds+K_P} \quad (7)$$

$$C_F(s)=\frac{\Theta(s)}{\tau_E(s)}=\frac{1}{Ms^2+K_Ds+K_P} \quad (8)$$

Where $C_P(s)$ and $C_V(s)$ are the position and velocity demand transfer functions respectively, and represent the effect of the position and velocity demand on the output of the system—position $\Theta(s)$. $C_F(s)$ is the force transfer function, which represents the effect of the external force.

The behaviour of the system can then be represented with $$\Theta(s)=C_P(s)\Theta_d(s)+C_V(s)\dot{\Theta}_d(s)+C_F(s)\tau_E(s) \quad (9)$$

2. Behaviour Inside the Free Region

Inside the safe region, the goal of the robot control is to allow free motion while retaining the surgeon's sense of feel for the hardness of the bone. To achieve that, the robots velocity can be controlled so it is proportional to the surgeon's guiding force:

$$\Theta_d=\Theta \quad (10)$$

$$\dot{\Theta}_d=AF_G \quad (11)$$

where $\dot{\Theta}_d$ is the portion of the Cartesian velocity demand transformed into joint space ($J^{-1}AF_G$), and A is admittance. Substituting Eq. (10) and $\tau_E=\tau_G$, where $\tau_G$ is the portion of the surgeon's guiding force affecting the joint ($J^TF_G$), into Eq. (9) yields $$\dot{\Theta}(s) = s\Theta(s) = \frac{1}{\frac{M}{K_D}s+1}\left(AF_G(s) + \frac{1}{K_D}\tau_G(s)\right) \quad (12)$$

It can be seen that this is a first order system which is asymptotically stable (since $K_D > 0$–negative feedback). The time constant $M/K_D$ decreases (and system's response becomes faster) with a lower inertia M and a higher $K_D$. Furthermore, a higher $K_D$ reduces the influence of $\tau_G$ compared to $AF_G$, which means that the velocity becomes a function of $F_G$ only. Higher A also reduces the influence of $\tau_G$ on velocity.

In the case of high inertia, a relatively high $K_D$ is required for a reasonable response, which in turn means a lower influence of $\tau_G$. On the other hand, a low inertia allows for lower $K_D$ (for the same response), which leads to a higher influence of $\tau_G$—i.e. the surgeon is effectively back-driving the robot.

Next, the ability to feel forces at the tip of the robot will be examined, which are not sensed by the force transducer (i.e. the cutting force). As a measure of that, the velocity changes that result from this force will be analysed. In reality, if a tip force is applied, the surgeon's "control algorithm" would compensate for lowered velocity by applying a higher guiding force, and, when cutting, this change of force is perceived as due to contact with a harder material.

With $F_G = 0$ and $\tau_G = \tau_T$, Eq. (12) becomes $$\dot{\Theta}(s) = s\Theta(s) = \frac{1}{\frac{M}{K_D}s+1}\frac{1}{K_D}\tau_T(s) \quad (13)$$

The steady state output can be determined with the help of final value theorem [Phillips, C L and Nagle, H T (1995). *Digital Control System Analysis and Design. Prentice-Hall*].

$$f(t=\infty) = \lim_{s\to 0} sf(s) \quad (14)$$

For a step tip force ($\tau_T(s) = \tau_T/s$) the steady state velocity is $$\dot{\Theta}(t=\infty) = \lim_{s\to 0} s\dot{\Theta}(s) = \frac{1}{K_D}\tau_T \quad (15)$$

A higher $K_D$ leads to a lower steady state velocity, which means that the surgeon's sensitivity to forces at the tip of the robot decreases. In conclusion, the dynamic behaviour of the system in the free region depends on M, $K_D$ and A. For a responsive system with the ability to feel forces, the following guidelines for the safe region should be followed:

The robot should be designed with low inertia M (and low friction)—i.e. a back-driveable robot;

Low derivative gain $K_D$—i.e. designed with the desired force sensitivity in mind; and The admittance A should be designed according to the desired guiding force range.

3. Behaviour at the Boundary

When the robot is at the boundary of the safe region, the motors should prevent any further motion into "no-go" region. Assume the robot is at the boundary and the surgeon is pushing towards the "no-go" region. To achieve this, the position and velocity demands can be set as $$\Theta_d = 0 \quad (16)$$

$$\dot{\Theta}_d = 0 \quad (17)$$

Note that $\Theta_d$ is set to the position of the boundary, which is 0. With these demands and $\tau_E = \tau_G$ (i.e. the portion of guiding force affecting the joint), Eq. (9) becomes $$\Theta(s) = \frac{1}{Ms^2 + K_D s + K_P}\tau_G(s) \quad (18)$$

For a step guiding force, the steady state position is $$\Theta(t=\infty) = \lim_{s\to 0} s\Theta(s) = \frac{1}{K_P}\tau_G \quad (19)$$

The position—which is a measure of boundary error—is proportional to $1/K_P$, and the robot behaves as a spring. The boundary error can be reduced by increasing $K_P$, which is, however, limited for stability resons. If the inertia of the robot is high, $K_P$ can be set to higher values, leading to a lower error. Note that integral gain could be used to reduce this error. However, this would not help in this case, since the material has already been machined away. A better solution is to compensate the guiding force, thus eliminating the cause of the error instead of reducing the error by setting high control gains.

4. Improved Active Constraint Control of the ACROBOT

Figure 18:
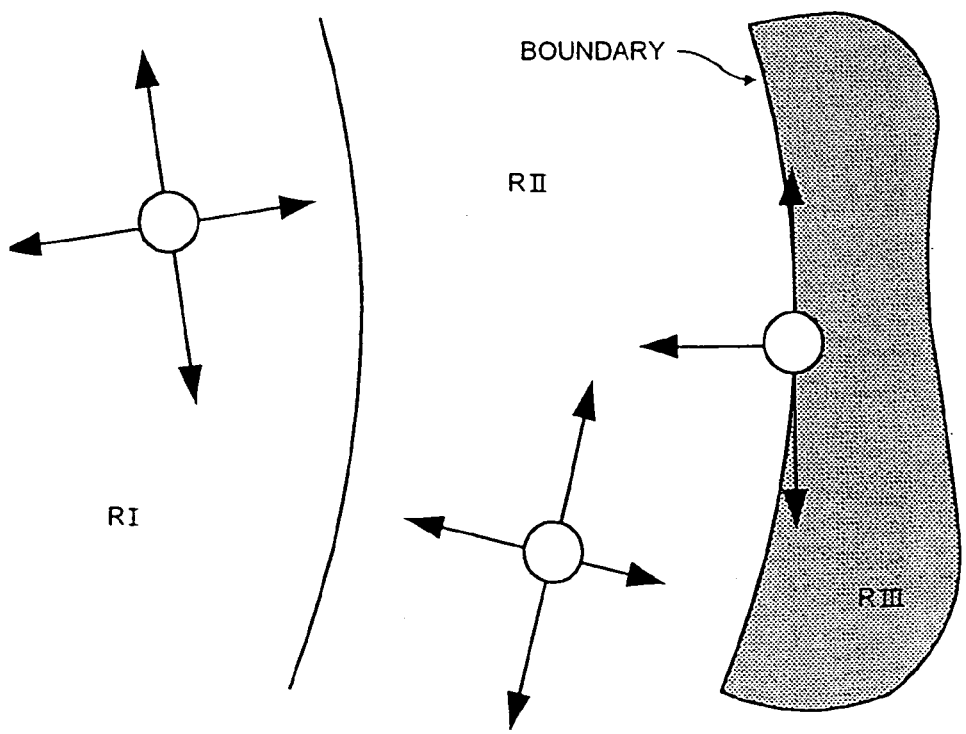
FIG. 18 shows a control principle under which the stiffness changes only in the direction towards the boundary.

The active control principle was modified to make the cutting process more useful and intuitive. The stiffness of the robot still changes according to the distance to the boundary in the same manner as before, by lowering the admittance A. However, the robot becomes stiffer only in the direction towards the boundary, while in other directions the stiffness is kept low as in the free region (see FIG. 18). This simple change of the boundary control algorithm significantly improves the task of guiding the robot. When near the boundary, the surgeon can move the cutter along or away from the boundary with a very low force. In addition, guiding-force compensation was introduced, which substantially reduces the over-boundary error.

The inner loop control law is similar to Eq. (2), but with added guiding force compensation $\tau_C$ (see Section 2), which is set by the boundary controller:

$$\tau = K_P(\Theta_d - \Theta) + K_D(\dot{\Theta}_d - \dot{\Theta}) + \tau_C + f^*(\Theta, \dot{\Theta}) + g^*(\Theta) \quad (20)$$

5. Boundary Controller

The boundary control law can be described as follows: First, the nearest point $X_{np}$ on the boundary is determined.

$$d = \|X - X_{np}\| = (X - X_{np}) \cdot N_{np} \quad (21)$$

where $N_{np}$ is the normal of the boundary at $X_{np}$, which is set to point inside the safe region. Inner loop control gains and demands depend on the d and are different in the three regions: Region I, II (inside the safe region) and III ("no-go" region). Note that Region II is necessary for stability reasons, since a rapid change of control parameters would result in a vibrating motion along the boundary.

Region I $d > D_1$

The control gains are low to allow the surgeon to feel the cutting forces.

Admittance is the same in all directions. The inner loop demands are set as $$\Theta_d = \Theta \quad (22)$$

$$\dot{\Theta}_d = J^{-1}(AF_G) \quad (23)$$

$$\tau_C = 0 \quad (24)$$

Region II $D_1 \geq d < 0$

The control gains increase as the distance to the boundary decreases. The inner loop position demand is the same as in Region II. If the guiding force points away from the boundary ($F_G \cdot N_{np} \geq 0$) the velocity demand and force compensation are also the same. Otherwise, the guiding force is split into normal ($F_{GN}$) and tangential ($F_{GT}$) components:

$$F_{GN} = (F_G \cdot N_{np}) N_{np} \quad (25)$$

$$F_{GT} = F_G - F_{GN} \quad (26)$$

and $\dot{\Theta}_d$ is comprised of two parts:

$$\dot{\Theta}_d = J^{-1}(A_N F_{GN} + AF_{GT}) \quad (27)$$

where $A_N$ is the admittance in normal direction, which decreases with distance to the boundary:

$$A_N = \frac{d}{D_1} A \quad (28)$$

The control is much more sensitive to the change of position control gains than to the amount of force compensation. The reason for this is that the guiding force changes at a much slower rate than the position and the velocity of the robot. This is true even when hitting a hard surface, due to the damping by the surgeon's arm.

Therefore, the amount of force compensation can be increased over a smaller region $D_2$. Guiding force compensation $\tau_C = 0$ if $d > D_2$, and increases over region $D_2 d > 0$:

$$\tau_C = -J^T \left( \frac{D_2 - d}{D_2} F_{GN} \right) \quad (29)$$

Region III: $d \leq 0$

The control gains are high in this region. The inner loop position demand is set to the nearest point:

$$\Theta_d = K^{-1} X_{np} \quad (30)$$

If the guiding force points away from the boundary, the $\Theta_d$ and $\tau_C$ are set as in Region I. Otherwise, the force is again split into normal and tangential directions, and the demands are set as $$\dot{\Theta}_d = J^{-1}(AF_{GT}) \quad (31)$$

$$\tau_C = -J^T F_{GN} \quad (32)$$

6. Implementation for a Planar Constraint

The improved control algorithm was first implemented for a planar constraint—a plane at an angle with the cutter. This simple constraint provides a good basis for testing the control and for empirical determination of control parameters. Apart from the modification of the control explained earlier in this section, the new implementation has some other advantages.

Firstly, the active constraint control program runs independently on a Nextmove DSP processor controller board, while the PC is used as a user interface, data storage and safety monitor. A special protocol was developed for a safe data transfer and communication between the two processors. This distribution of functions allows all the processing power of the DSP to be used only for the control algorithm, which improves the speed of the control loop. Further, the program becomes much simpler and easier to test and debug. Along with the safety monitor function of the PC, this substantially increases the safety of the system.

Another advantage is that the main control loop is executed in global (Cartesian) coordinates. All joints are therefore used equally for the boundary control, eliminating the stepping problem of earlier implementations.

Further, the control is implemented as a true two-level control. The position control loop is a simple interrupt routine, which is executed every 2 ms. It implements a simple PD control algorithm for each joint with gravity, friction and guiding force compensation—Eq. (20). The main control loop is more computationally intensive, since it includes coordinate transformations, force sensor handling and boundary control (see Section 5), and therefore runs at a lower speed (approximately 10 ms). The high speed of the position control loop ensures a stable control during the computation period of the main loop.

Cutting experiments showed good results for planes, inclined at any angle.

7. 2.5-D Boundary Constraint

Figure 19:
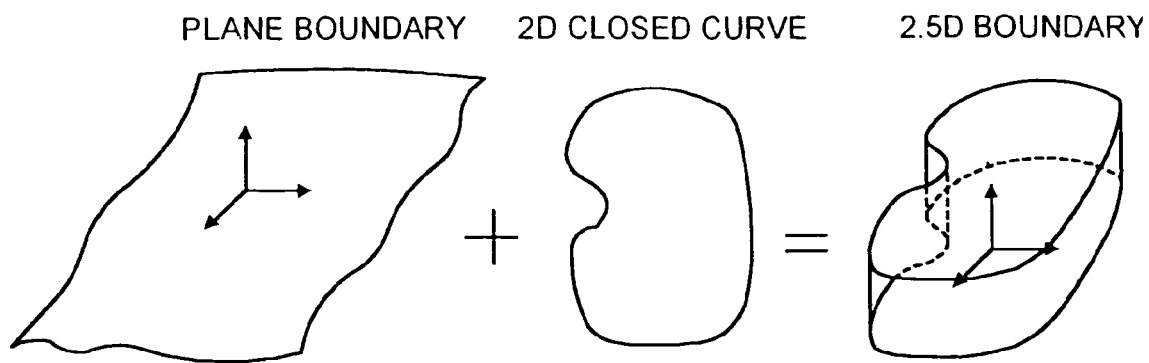
FIG. 19 illustrates what is meant by "2.5-D constraint"

The plane boundary was extended into the 3rd dimension by applying a 2-D closed curve constraint as an outside constraint, which is used to protect the soft tissue next to the bone. As will be seen from FIG. 19, the expression "2.5-D" is, in this document, used to signify an extruded 2D shape. This is adequate for the nature of the prosthesis used, where the required surface can be produced by cutting flat planes in sequence. Initially, the same control algorithm as for a plane boundary was used. This, however, resulted in instabilities near the intersecting edge between the outside and plane boundaries. The problem was explored in detail to find the cause.

8. Instability at a Sharp Edge

Figure 20:
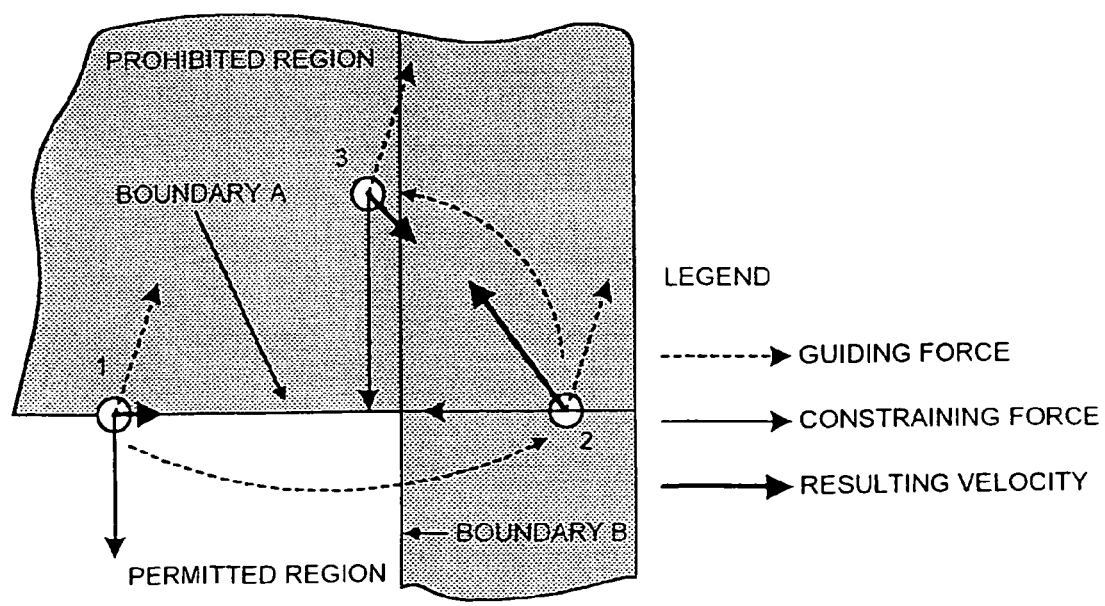
FIG. 20 shows instability at a sharp edge.

When moving across the intersecting edge, the normal to the boundary instantly changes direction by 90°, since the outside and the plane boundaries intersect at 90°. This also means that the constraining force instantly changes direction, which subsequently leads to instabilities in the control. FIG. 20 shows the principle of the problem on an example, where the cutter was pushed with a constant guiding force along boundary section A towards boundary section B, which intersect at 90°.

The speed of approaching the edge is of a great importance. The faster the cutter approaches the edge along the boundary section A (situation 1), the further over the boundary section B (situation 2) it will go before the controller reacts (due to delays in the control loop). The size of the constraining force depends on this over-boundary error. Greater error leads to greater reaction force, which can force the cutter to bounce back into the region before the edge, which is dominated by the boundary section A (situation 3). In that case, the normal switches its direction again and the whole process can be repeated, resulting in undesirable vibrations at the edge. The problem also evolves near sharply curved surfaces, whose normal vector changes direction within a relatively small area compared to the length of Region II. In other words, if only the nearest point is considered when adjusting $\dot{X}_d$ (velocity demand), $\dot{X}_d$ is discontinuous when the normal at the nearest point changes.

Figure 21:
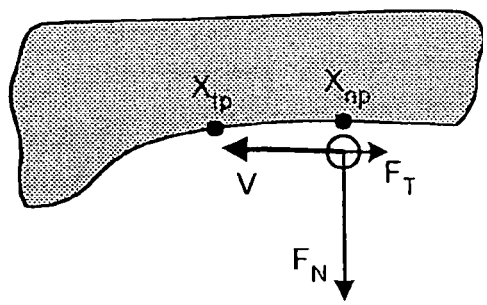
FIGS. 21 and 22 illustrate adjustment of the tangential stiffness for a 2-D boundary.
Figure 22:
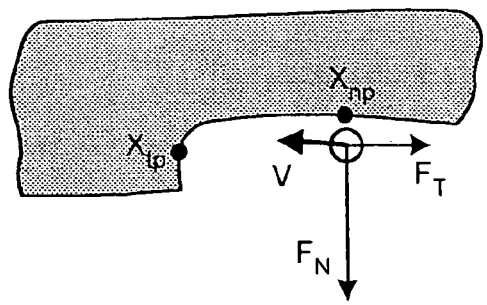

Therefore, the goal is to define the desired velocity $X_d$ so that it is continuous in the whole workspace. One way to ensure that, is to adjust $_d$ to be the same in all directions ($A_T$ is the same as $A_N$). This however leads to difficult motion along the boundary. A better solution is to limit the tangential velocity of the cutter near such features of the boundary. In other words, the robot has to become stiffer in the tangential direction, depending on the distance to such a feature. FIGS. 21 and 22 show how the tangential stiffness should be adjusted for two different shapes of 2-D boundaries.

Generally, the stiffness (or the amount of the tangential constraining force) depends upon the shape or curvature of the constraint surface within a (pre-defined) region that surrounds the tool tip.

The normal stiffness and constraining force ($F_N$) depend on the distance to the nearest point ($X_{np}$)—same as for a plane constraint. The tangential stiffness, which ensures the stability at the edges, is adjusted according to the neighboring/adjacent surface. A particular point on the surface affects the stiffness according to the distance of the point to the cutter and the angle of the normal to the surface in that point. A smaller distance results in greater stiffness. Similarly, a smaller angle between the direction of adjusting the stiffness and the normal, results in a greater stiffness. The tangential stiffness is chosen as the greatest value from the calculations of every point on the surface. In FIGS. 21 and 22 the most influential point for tangential stiffness is labelled $X_{tp}$. Because the surface is less curved in the first example, the tangential constraining force ($F_T$) is lower, leading to higher velocity (V). Alternatively, the stiffness could be based on the length of the tangential vector between the tip of the tool and the point at which it intersects the constraint surface.

9. 2-D Boundary Outline

A modified boundary control strategy is proposed here for a 2.5-D boundary, which also controls the stiffness in the tangential direction. The concept is to split the guiding force into three orthogonal components and to adjust the stiffness separately in each of those directions. The stiffness is adjusted not only according to the minimum distance to the boundary, but according to the whole neighboring surface in the sphere with radius of Region II. For a 2.5-D boundary, this is a quite straightforward process, since the task can be divided into two independent parts: a 1-D problem (distance to the plane boundary) and a 2-D problem (outside boundary). For a plane boundary, the stiffness in the direction towards the plane can be adjusted as explained in Section 5. The stiffness in the other two orthogonal directions can be adjusted according to the outside boundary as follows.

One way of representing a 2-D boundary outline is with B-spline curves. However, this representation would require a relatively large amount of processing if it was implemented for active constraint control. Due to a limited computation power of the DSP processor on the controller board, a better approach is to approximate the 2-D curve with a series of points on the curve, connected with line segments. The higher the number of points n, the more accurate the representation, but the longer the processing time. A compromise can be reached, where the curve is represented with a sufficient accuracy and the number of points is low enough to allow a reasonably short time delay of the boundary control algorithm.

Figure 23:
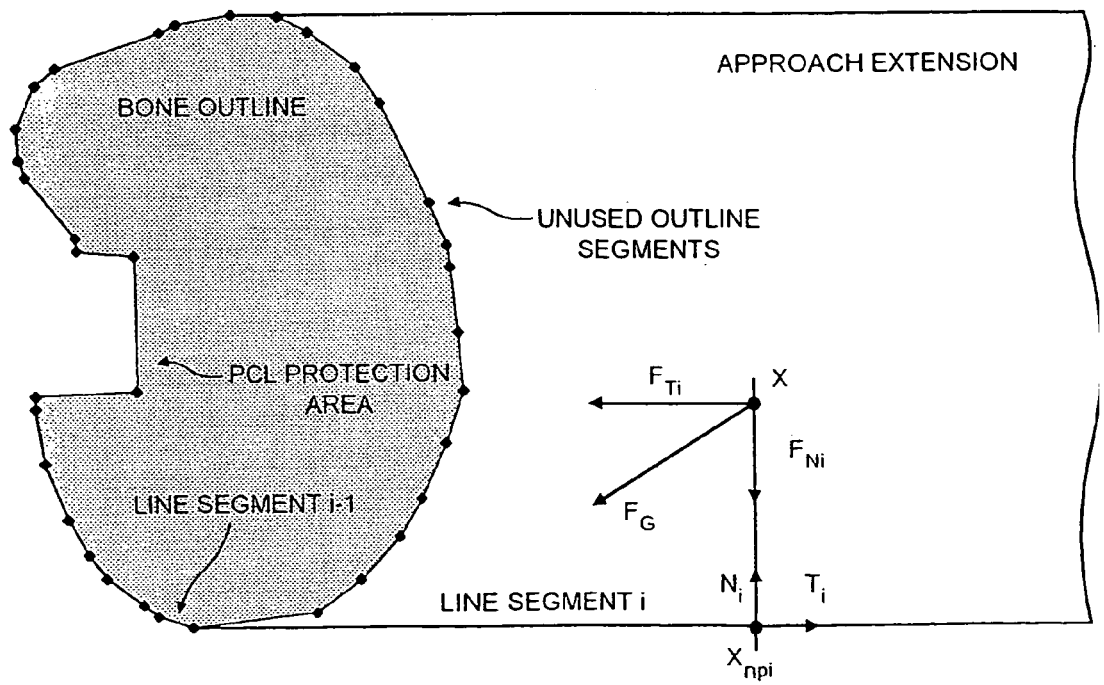
FIG. 23 shows a 2-D outline of the constraint for preparing the surface of the tibia.

The strategy discussed in Section 5 works well for a planar constraint and can also be applied without modification for a convex 2-D curve, since the tangential stiffness is not limited. However, for the bone surface preparation a closed outline is necessary to protect the surrounding tissue. FIG. 23 shows an outline for preparing the tibia for the prosthesis component, with an extension of the bone outline to allow the robot to approach the bone from the front. The outlines for other surfaces (i.e. on the femur) are similar. The line segment i, if considered separately, affects $\dot{X}_d$ only in the direction of the normal of that segment ($N_i$):

$$\dot{X}_{dNi} = A_{Ni}(F_G \cdot N_i)N_i = A_{Ni}F_{Ni} \tag{33}$$

where $A_{Ni}$ depends on the distance to the nearest point on that segment and is equal to A if $F_G$ points away from that segment (see Section ?). If all line segments are considered, the velocity demand can be chosen as the maximum $X_d$ that satisfies the condition $$\dot{X}_d \cdot N_i \leq A_{Ni}(F_G \cdot N_i) \tag{34}$$

for each line segment $I \in \{1, 2, \ldots, n\}$.

The procedure is as follows: First, the segment m with minimum $A_{Nm} = \min\{A_{Ni}\}$ is found. $A_{Nm}$ corresponds to the closest point on the curve in the half-plane defined by the direction of $F_G$. The guiding force can then be separated in two directions—normal and tangential to that segment:

$$F_G = (F_G \cdot N_m)N_m + (F_G \cdot T_m)T_m = F_{Nm}N_m + F_{Tm}T_m \tag{36}$$

The velocity demand can then be formed from each of the two components as $$\dot{X}_d = A_{Nm}F_{Nm}N_m + A_T F_{Tm}T_m \tag{36}$$

Where $A_T$ can be any tangential admittance, since it does not affect condition ? for m-th segment. Substituting Eq. (36) into condition (34) yields $$(A_{Nm}F_{Nm}N_m + A_{Ti}F_{Tm}T_m) \cdot N_i \leq A_{Ni}F_G \cdot N_i \tag{37}$$

and a maximum possible $A_{Ti}$ for segment i can be derived:

$$A_{Ti} = \frac{A_{Ni}(F_G \cdot N_i) - A_{Nm}F_{Nm}(N_m \cdot N_i)}{F_{Tm}(T_m \cdot N_i)} \tag{38}$$

To satisfy condition (37) for all segments $I \in \{1, 2, \ldots, n\}$, $A_T$ is chosen as the minimum tangential admittance $A_T = \min\{A_{Ti}\}$.

If the 2-D curve includes concave surface parts (e.g. PCL protection area in FIG. 23), the above procedure could lead to incorrect tangential admittance. To avoid this, only the part of the line is considered that actually forms a surface. The other part is replaced by the point of the intersection of the two lines.

Figure 24:
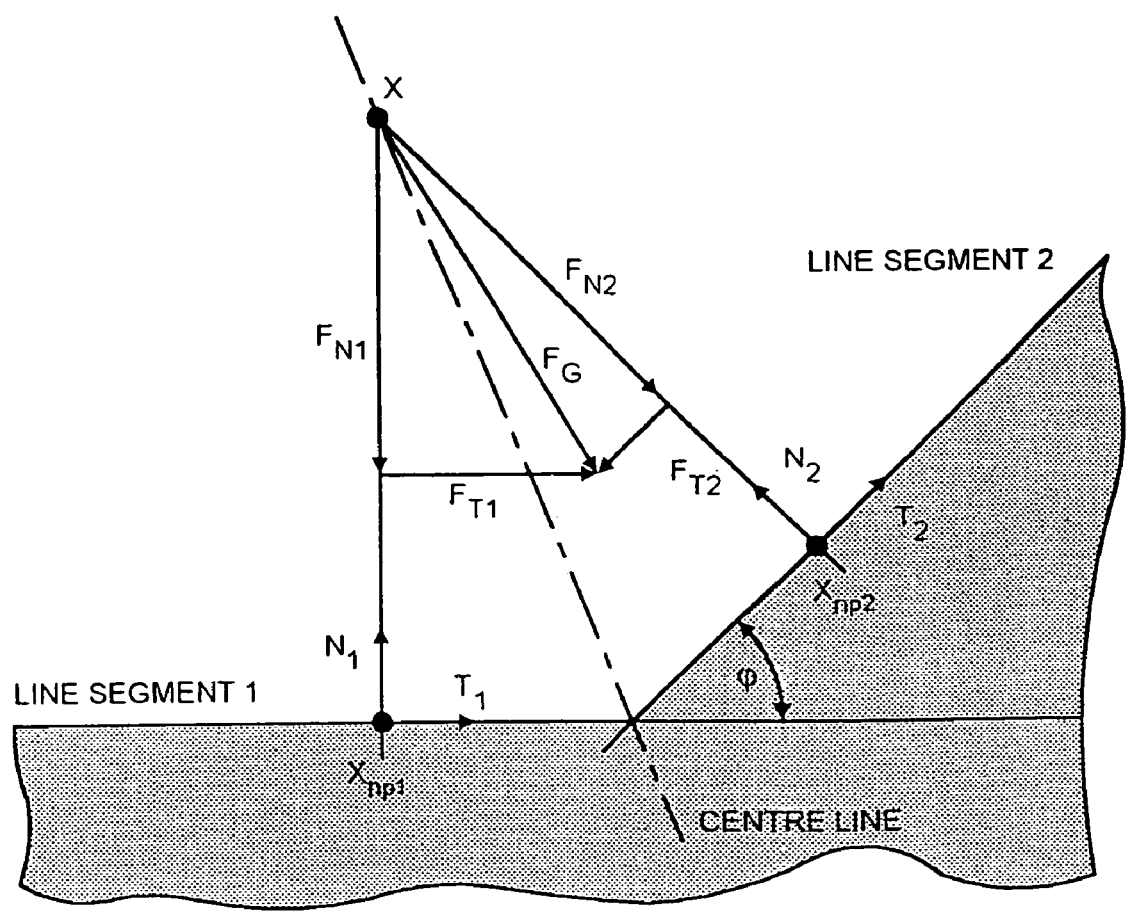
FIG. 24 shows two line segments at an angle.

As seen in Section 8, an instability occurs if $\dot{X}_d$ is not continuous in the whole workspace. To prove that $\dot{X}_d$ as defined above is continuous, an edge formed of two line segments at an angle $\Phi$ will be examined (FIG. 24). The problem can appear at the centre line of the edge, since the nearest point changes from one segment to the other. This results in a different direction of $N_m$, which might lead to a different $\dot{X}_d$ at the centre line, depending on which segment is used in the first step of the procedure.

Assume that the position of the robot is on the centre line of the edge and the nearest point is on segment 1. Note, that $A_{N1}=A_{N2}=A_N$, since the distance to both segments is the same. The velocity demand is $$\dot{X}_d = A_N F_{N1} N_1 + A_T F_{T1} T_1 \quad (39)$$

and the tangential admittance, defined by segment 2 is $$A_T = \frac{A_N(F_G \cdot N_2) - A_N F_{NI}(N_1 \cdot N_2)}{F_{TI}(T_1 \cdot N_2)} \quad (40)$$

The relationship between the normals and tangents of the two segments can be expressed as $$N_2 = \cos \Phi N_1 - \sin \Phi T_1 \quad (41)$$

$$T_2 = \sin \Phi N_1 + \cos \Phi T_1 \quad (42)$$

and $$N_1 \cdot N_2 = \cos \Phi \quad (43)$$

$$T_1 \cdot N_2 = -\sin \Phi \quad (44)$$

which after some manipulation leads to $$A_T = A_N \quad (45)$$

This means that the admittance at the centre line is the same in both directions, and the order of computation is not important. Therefore, $\dot{X}_d$ is continuous at the centre line and in the whole workspace.

The 2.5-D algorithm was implemented on the ACROBOT's DSP controller board, which was able to execute the algorithm at a rate of approximately 100 Hz (10 ms cycle time) for a typical TKR surface. The guiding of the robot was smooth, intuitive, and stable, without any undesired "shaking" at sharp corners of the boundary, even with high guiding forces applied.

It is expected that a similar approach—that is, in which the tangential stiffness depends on the shape of the neighboring surface—will apply to true 3D implementations.

Finally, it will be understood that the present invention has been described in its preferred embodiments and can be modified in many different ways without departing from the scope of the invention as defined by the appended claims.

The invention claimed is:

1. A method of controlling an active-constraint robot, comprising:
   providing an active-constraint robot (4) including a tool (14) for operating on element, and a drive unit (20,28, 38) for controlling movement of the tool;
   providing a model including a NURBS surface describing a constraint surface associated with the element;
   determining the imaginary point (I) of intersection of a force vector (V) representative of a force applied by a user to the tool and the NURBS surface; and
   controlling the drive unit (20,28,38) by resisting movement of the tool according to the determined point of intersection.

2. A method as claimed in claim 1 in which the NURBS surface is tessellated in determining the point (I) of intersection.

3. A method as claimed in claim 2 in which tessellations of a first resolution and at least one higher, second resolution are generated, the tessellations of the first resolution enabling a first determination of the point (I) of intersection and the tessellations of the second resolution enabling a second, more accurate, determination of the point (I) of intersection.

4. A method as claimed in any one of the preceding claims in which movement is resisted by applying a constraining force which is a function of the distance between the imaginary point of intersection and the tool (14), and of the force being applied by the user.

5. A method of controlling an active-constraint robot, comprising:
   providing an active-constraint robot (4) including a tool (14) for operating on element, and a drive unit (20,28, 38) for controlling movement of the tool;
   providing a model including a model surface describing a constraint surface associated with the element;
   determining the imaginary point (I) of intersection of a force vector (V) representative of a force applied by a user to the tool and the model surface; and
   controlling the drive unit (20,28,38) by resisting movement of the tool according to the determined point of intersection.

6. A method as claimed in claim 5 in which the model surface is tessellated in determining the point (I) of intersection.

7. A method as claimed in claim 6 in which tessellations of a first resolution and at least one higher, second resolution are generated, the tessellations of the first resolution enabling a first determination of the point (I) of intersection and the tessellations of the second resolution enabling a second, more accurate, determination of the point (I) of intersection.

8. A method as claimed in any one of claims 5 to 7 in which movement is resisted by applying a constraining force which is a function of the distance between the imaginary point of intersection and the tool (14), and of the force being applied by the user.

9. An active-constraint robot (4) including:
   a tool (14) for operating on an element;
   a drive unit (20,28,38) for controlling movement of the tool;
   means for holding a model including a NURBS surface describing a constraint surface associated with the element;
   means for determining the imaginary point (I) of intersection of a force vector (V) representative of a force applied by a user to the tool and the NURBS surface; and
   a control for controlling the drive unit (20,28,38) by resisting movement of the tool according to the determined point of intersection.

10. A robot as claimed in claim 9 including means for tessellating the NURBS surface in determining the point (I) of intersection.

11. A robot as claimed in claim 10 in which tessellations of a first resolution and at least one higher, second resolution are generated, the tessellations of the first resolution enabling a first determination of the point (I) of intersection and the tessellations of the second resolution enabling a second, more accurate, determination of the point (I) of intersection.

12. A robot as claimed in any one of claims 9 to 11 in which the controller resists movement by applying a constraining force which is a function of the distance between the imaginary point of intersection and the tool (14), and of the force being applied by the user.

13. An active-constraint robot (4) including:
   a tool (14) for operating on an element and a drive unit (20,28,38) for controlling movement of the tool;
   means for holding a model including a model surface describing a constraint surface associated with the element;
   means for determining the imaginary point (I) of intersection of a force vector (V) representative of a force applied by a user to the tool and the model surface; and
   a control for controlling the drive unit (20,28,38) by resisting movement of the tool according to the determined point of intersection.

14. A robot as claimed in claim 13 including means for tessellating the model surface in determining the point (I) of intersection.

15. A robot as claimed in claim 14 in which tessellations of a first resolution and at least one higher, second resolution are generated, the tessellations of the first resolution enabling a first determination of the point (I) of intersection and the tessellations of the second resolution enabling a second, more accurate, determination of the point (I) of intersection.

16. A robot as claimed in any one of claims 13 to 15 in which the controller resists movement by applying a constraining force which is a function of the distance between the imaginary point of intersection and the tool (14), and of the force being applied by the user.

17. A method of controlling an active-constraint robot, comprising:
   providing an active constraint robot (4) including a tool (14) for operating on an element, and a drive unit (20,28,38) for controlling movement of the tool;
   providing a model describing a constraint surface associated with the element; and
   controlling the drive unit by resisting movement of the tool in a direction tangential to an adjacent constraint surface in dependence upon the shape of the constraint surface in a region surrounding the position of the tool.

18. A method as claimed in claim 17 in which the tangential direction is defined as that direction perpendicular to the shortest line normal to the constraint surface which intersects the tool.

19. A method as claimed in claim 18 in which the amount of resistance is dependent upon the length of the tangential vector between the tool and a point at which it intersects the constraint surface.

20. A method as claimed in claim 17 or claim 18 in which a plurality of points lying on the surface and within the region are considered, the amount of constraint being a function of the distance of each point to the tool and the angle between a normal to the surface at each point and a line extending between each said point and the tool.

21. A method as claimed in claim 20 in which a separate value is calculated for each said point, with the amount of resistance applied to the tool being set at the maximum value for all the said points.

22. A method as claimed in claim 17 or claim 18 in which a separate resistance value is calculated for a plurality of points lying on the surface and within the region, the amount of resistance applied to the tool being determined in dependence upon the largest of the said separate resistance values.

23. An active constraint robot (4) including:
   a tool (14) for operating on an element;
   a drive unit (20,28,38) for controlling movement of the tool;
   means for holding a model describing a constraint surface associated with the element; and
   control means for controlling the drive unit by resisting movement of the tool in a direction tangential to an adjacent constraint surface in dependence upon the shape of the constraint surface in a region surrounding the position of the tool.

24. A robot as claimed in claim 23 in which the tangential direction is defined as that direction perpendicular to the shortest line normal to the constraint surface which intersects the tool.

25. A robot as claimed in claim 24 in which the amount of resistance is dependent upon the length of the tangential vector between the tool and a point at which it intersects the constraint surface.

26. A robot as claimed in claim 23 or claim 24 in which the control means considers a plurality of points lying on the surface and within the region, the amount of constraint being a function of the distance of each point to the tool and the angle between a normal to the surface at each point and a line extending between each said point and the tool.

27. A robot as claimed in claim 26 in which a separate value is calculated for each said point, with the amount of resistance applied to the tool being set at the maximum value for all the said points.

28. A robot as claimed in claim 23 or claim 24 in which the control means calculates a separate resistance value for a plurality of points lying on the surface and within the region, the amount of resistance applied to the tool being determined in dependence upon the largest of the said separate resistance values.

* * * * *